United States Patent
Li et al.

(10) Patent No.: US 6,375,819 B1
(45) Date of Patent: Apr. 23, 2002

(54) FLUID DELIVERY SYSTEM FOR CAPILLARY ELECTROPHORETIC APPLICATIONS

(75) Inventors: Qingbo Li; Changsheng Liu; Thomas E. Kane, all of State College; John R. Kernan, Loganton, all of PA (US); Bernard Sonnenschein, Brooklyn, NY (US); Michael V. Sharer, Tyrone, PA (US)

(73) Assignee: Spectrumedix Corporation, State College, PA (US)

( * ) Notice: Subject to any disclaimer, the term of this patent is extended or adjusted under 35 U.S.C. 154(b) by 0 days.

(21) Appl. No.: 09/373,909

(22) Filed: Aug. 13, 1999

Related U.S. Application Data

(62) Division of application No. 09/105,988, filed on Jun. 29, 1998.
(60) Provisional application No. 60/053,836, filed on Jun. 30, 1997.

(51) Int. Cl.[7] ............... G01N 27/26; G01N 27/447
(52) U.S. Cl. ............... 204/455; 204/451; 204/452; 204/453; 204/601; 204/603; 204/604; 204/605; 222/132; 222/144.5; 222/145.1; 141/31; 141/104
(58) Field of Search ................ 204/451, 452, 204/453, 454, 455, 601, 602, 603, 604, 605; 137/565.35; 122/135, 132, 136, 145.1, 144.5; 141/31, 104

(56) References Cited

U.S. PATENT DOCUMENTS

| | | | |
|---|---|---|---|
| 5,085,757 A | 2/1992 | Karger et al. | 204/603 |
| 5,198,091 A | 3/1993 | Burolla et al. | 204/601 |
| 5,235,409 A | 8/1993 | Burgi et al. | 356/436 |

(List continued on next page.)

FOREIGN PATENT DOCUMENTS

| | | |
|---|---|---|
| DE | 90 11 484.1 | 11/1990 |
| EP | 0 257 855 A2 | 3/1988 |
| EP | 0 723 149 A2 | 7/1996 |

(List continued on next page.)

OTHER PUBLICATIONS

International Search Report, Appl. No. PCT/US98/13667, mailed Oct. 30, 1998.
Written opinion in corresponding International Application No. PCT/US98/13667 (WO 99/00664).

*Primary Examiner*—Jill Warden
*Assistant Examiner*—John S. Starsiak, Jr.
(74) *Attorney, Agent, or Firm*—Pennie & Edmonds LLP

(57) ABSTRACT

An automated electrophoretic system is disclosed. The system employs a capillary cartridge having a plurality of capillary tubes. The cartridge has a first array of capillary ends projecting from one side of a plate. The first array of capillary ends are spaced apart in substantially the same manner as the wells of a microtitre tray of standard size. This allows one to simultaneously perform capillary electrophoresis on samples present in each of the wells of the tray. The system includes a stacked, dual carrousel arrangement to eliminate cross-contamination resulting from reuse of the same buffer tray on consecutive executions from electrophoresis. The system also has a gel delivery module containing a gel syringe/a stepper motor or a high pressure chamber with a pump to quickly and uniformly deliver gel through the capillary tubes. The system further includes a multi-wavelength beam generator to generate a laser beam which produces a beam with a wide range of wavelengths. An off-line capillary reconditioner thoroughly cleans a capillary cartridge to enable simultaneous execution of electrophoresis with another capillary cartridge. The streamlined nature of the off-line capillary reconditioner offers the advantage of increased system throughput with a minimal increase in system cost.

20 Claims, 29 Drawing Sheets

U.S. PATENT DOCUMENTS

| | | | |
|---|---|---|---|
| 5,240,585 A | 8/1993 | Young et al. | 204/601 |
| 5,274,240 A | 12/1993 | Mathies et al. | 250/458.1 |
| 5,277,780 A | 1/1994 | Kambara | 204/603 |
| 5,332,480 A | 7/1994 | Datta et al. | 204/451 |
| 5,332,481 A | 7/1994 | Guttman | 204/455 |
| 5,356,525 A * | 10/1994 | Goodale et al. | 204/602 |
| 5,413,686 A * | 5/1995 | Klein et al. | 204/603 |
| 5,417,925 A | 5/1995 | Goodale et al. | 422/103 X |
| 5,436,130 A | 7/1995 | Mathies et al. | 435/6 |
| 5,498,324 A | 3/1996 | Yeung et al. | 204/452 |
| 5,605,666 A | 2/1997 | Goodale et al. | 422/103 |
| 5,635,050 A | 6/1997 | Pentoney, Jr. et al. | 204/605 |
| 5,730,850 A | 3/1998 | Kambara et al. | 204/603 |
| 5,885,430 A * | 3/1999 | Kernan et al. | 204/453 |
| 5,963,456 A * | 10/1999 | Klein et al. | 364/496 |
| 6,027,627 A * | 2/2000 | Li et al. | 204/603 |
| 6,063,251 A * | 5/2000 | Kane et al. | 204/601 |

FOREIGN PATENT DOCUMENTS

| | | |
|---|---|---|
| GB | 2 113 903 A | 8/1983 |
| WO | WO 89/04966 | 6/1989 |
| WO | WO 94/29712 | 12/1994 |
| WO | WO 94/29713 | 12/1994 |

* cited by examiner

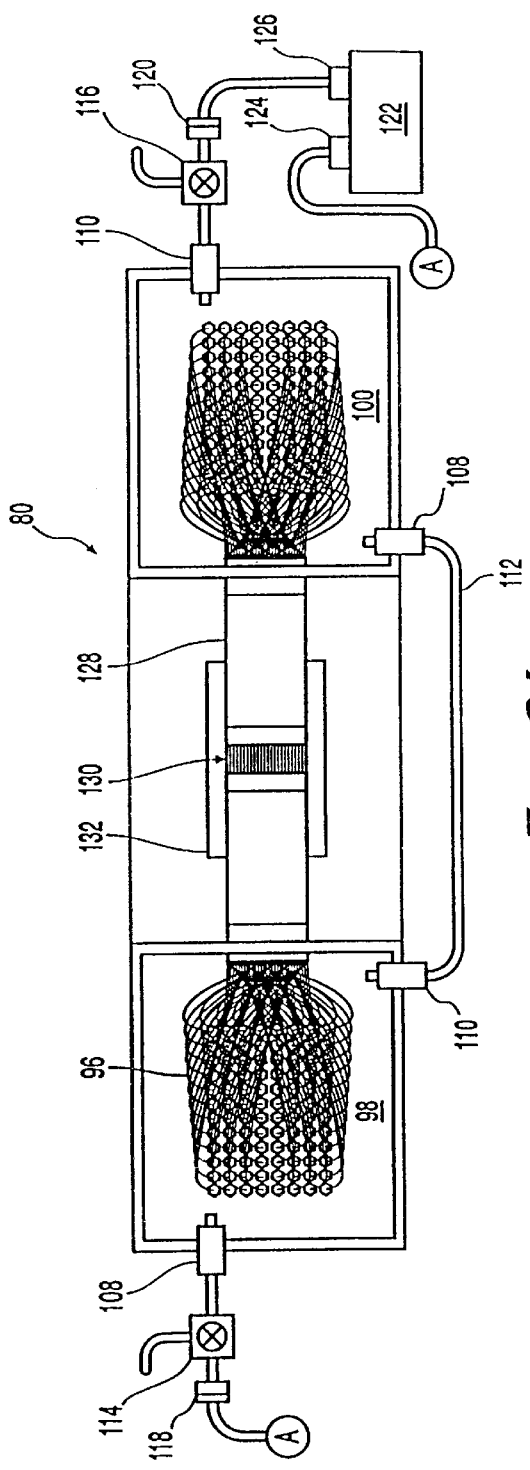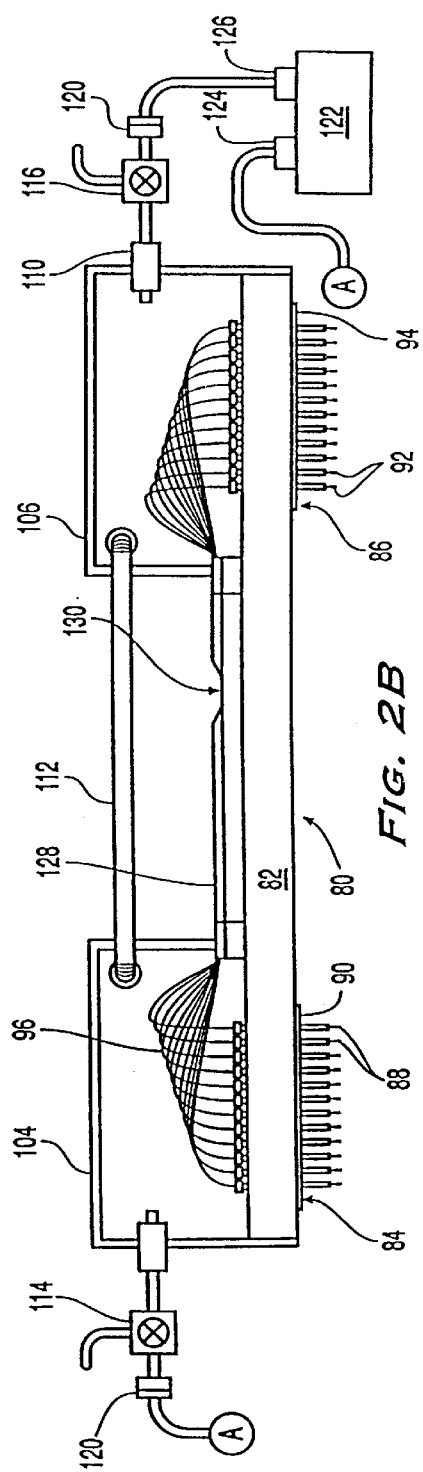

FLUID DELIVERY SYSTEM FOR CAPILLARY ELECTROPHORETIC APPLICATIONS

RELATED APPLICATIONS

This is a divisional of application Ser. No. 09/105,988, filed Jun. 29, 1998, which claims priority to U.S. Provisional application No. 60/053,836, filed Jun. 30, 1997.

TECHNICAL FIELD

This invention relates to an apparatus for performing electrophoresis. More particularly, it pertains to an automated electrophoresis system employing capillary cartridges which are configured for use with commercially available, microtitre trays of standard size and including a stacked, dual carrousel arrangement, a multi-wavelength beam generator, a gel delivery system and an off-line reconditioner to eliminate cross-contamination of samples, improve system capacity and increase system throughput.

BACKGROUND

Electrophoresis is a well-known technique for separating macromolecules. In electrophoretic applications, molecules in a sample to be tested are migrated in a medium across which a voltage potential is applied. Oftentimes, the sample is propagated through a gel which acts as a sieving matrix to help retard and separate the individual molecules as they migrate.

One application of gel electrophoresis is in DNA sequencing. Prior to electrophoresis analysis, the DNA sample is prepared using well-known methods. The result is a solution of DNA fragments of all possible lengths corresponding to the same total sequential order, with each fragment terminated with a tag label corresponding to the identity of the given terminal base.

The separation process employs a capillary tube filled with conductive gel. To introduce the sample, one end of the tube is placed into the DNA reaction vial. After a small amount of sample enters the capillary end, both capillary ends are then placed in separate buffer solutions. A voltage potential is then applied across the capillary tube. The voltage drop causes the DNA sample to migrate from one end of the capillary to the other. Differences in the migration rates of the DNA fragments cause the sample to separate into bands of similar-length fragments. As the bands traverse the capillary tube, the bands are typically read at some point along the capillary tube using one of several detection techniques.

The most popular fluorescent dyes for tag labeling the DNA samples have absorption maximum wavelength ranging from 490–580 nm. A basic detection technique consists of a CCD camera with a wide-angle lens, a capillary tube array placed under the camera lens with its planar surface parallel to the CCD imaging chip, and a laser beam illuminating across the capillary array. However, a single laser line provided in the basic detection technique cannot favor all of the tag labels at the same time; therefore, either multiple lasers or optical filters are used to compensate for this shortcoming.

Usually, multiple DNA preparation reactions are performed in a commercially available microtitre tray having many separate low-volume wells, each holding on the order of 200–1000 micro-liters. The microtitre trays come in standard sizes. In the biotech industry, the currently preferred microtitre tray has a rectangular array comprising of 8 rows and 12 columns of wells. The centers of adjacent wells found in a single row are separated by approximately 0.9 cm, although this figure may vary by one or two tenths of a millimeter. The same holds for the spacing between adjacent wells in a single column. The rectangular array of 96 wells has a footprint within an area less than 7.5 cm×11 cm.

Miniaturization has allowed more wells to be accommodated in a single microtitre tray having the same footprint. New trays having four times the density of wells within the same footprint have already been introduced and are fast becoming the industry standard. Thus, these new trays have 16 rows and 24 columns with an inter-well spacing of approximately 0.45 cm.

It is not uncommon to analyze several thousand DNA samples for a given DNA sequencing project. Needless, to say, it is time consuming to employ a single capillary tube for several thousand runs.

Prior art devices have suggested means for analyzing DNA bands in multiple capillaries simultaneously. Such a device is disclosed in U.S. Pat. No. 5,498,324 to Yeung et al, whose contents are incorporated by reference in their entirety. This reference teaches a means for detecting the DNA bands as they are separated in multiple capillary tubes which are positioned parallel to another. However, in such an arrangement, each capillary tube is filled with gel and a sample is introduced into each capillary tube.

The arrangement described above takes a considerable amount of time to fill each capillary tube with gel. It also takes considerable effort to introduce a reaction sample into one end of each of the tubes reproducibly and reliably.

It is also not uncommon that one uses the same capillary tube for several consecutive sample runs. This, obviously risks cross-contamination of samples, which is a further disadvantage in certain prior art arrangements.

SUMMARY OF THE INVENTION

One object of the invention is to provide a device which allows one to simultaneously introduce samples into a plurality of capillary tubes directly from microtitre trays having a standard size.

Another object of the invention is to provide a stacked, dual carrousel arrangement to eliminate cross-contamination of DNA samples without reducing system capacity.

Another object of the invention is to provide a gel delivery module to uniformly distribute gel through the capillary tubes quickly.

Another object of the invention is to provide an off-line capillary reconditioner to thoroughly clean a capillary cartridge off-line to improve system throughput with a minimal increase in cost.

Another object of the invention is to provide an apparatus that produces a multi-wavelength beam. This multi-wavelength beam apparatus allows simultaneous detection of DNA samples which are tagged with different fluorescent tag labeling dyes.

These objects are achieved by a disposable capillary cartridge which can be cleaned between electrophoresis runs, the cartridge having a plurality of capillary tubes. A first end of each capillary tube is retained in a mounting plate, the first ends collectively forming an array in the mounting plate. The spacing between the first ends corresponds to the spacing between the centers of the wells of a microtitre tray having a standard size. Thus, the first ends of the capillary tubes can simultaneously be dipped into the samples present in the tray's wells. The cartridge is provided with a second mounting plate in which the second ends of the capillary tubes are retained. In another embodiment, instead of the second mounting plate, the second ends of the capillary tubes are bundled together and received by a liquid delivery chamber, preferably a high pressure T-fitting.

Plate holes may be provided in each mounting plate and the capillary tubes inserted through these plate holes. In such case, the plate holes are sealed airtight so that the side of the mounting plate having the exposed capillary ends can be pressurized. Application of a positive pressure in the vicinity of the capillary openings in this mounting plate allows for the introduction of air and fluids during electrophoretic operations and also can be used to force out gel and other materials from the capillary tubes during reconditioning. The capillary tubes may be protected from damage using a needle comprising a cannula and/or plastic tubes, and the like when they are placed in these plate holes. When metallic cannula or the like are used, they can serve as electrical contacts for current flow during electrophoresis.

In the preferred embodiment, a stacked, dual carrousel arrangement eliminates a cross-contamination problem without reducing the capacity of the system. The system uses a buffer solution with the gel to provide a medium for the migration of DNA from one end of the capillary tubes to the other end during electrophoresis. Since the buffer solution also migrates through the capillary tubes during electrophoresis, one end of the capillary tubes must be immersed in buffer solution to continuously replenish the buffer supply in the capillary tubes. Accordingly, the buffer solution may become contaminated with the DNA sample during electrophoresis. Next, the DNA in the buffer solution could migrate into the capillary tubes during a subsequent execution of electrophoresis if the same buffer solution is used on consecutive executions of electrophoresis. The stacked, dual carrousel arrangement eliminates this contamination problem by providing a buffer tray for each DNA sample tray to avoid reuse of the same buffer tray. Since the stacked, dual carrousel arrangement has an additional carrousel to hold the buffer trays, the arrangement does not have to displace any sample trays to provide room for the additional buffer trays. Thus, the arrangement eliminates the contamination problem without reducing system capacity.

In another aspect of the preferred embodiment of this invention, the detection system employs both a multi-wavelength beam generator and multi-wavelength detector in order to allow DNA sequencing samples tagged with different labeling dyes to be detected simultaneously in the same instrument without switching laser or optical filters.

The multi-wavelength beam generator is provided by an argon ion laser capable of producing multi-wavelength beam with wavelengths at 457 nm, 476 nm, 488 nm, 496 nm, 502 nm, 514 nm. The multi-wavelength beam generator compensates for the different absorption spectra among the different labeling dyes, improves the peak detection signal evenness among DNA fragments and enhances the signal to noise ratio of the detection signal.

In another aspect of the preferred embodiment, a gel delivery module quickly and uniformly delivers gel through the capillary tubes. Since the gel is too viscous to be delivered by a pump, the gel delivery module uses a gel syringe to deliver the gel. The gel delivery module includes a gel carriage to hold a disposable gel cartridge. A stepper motor linear actuator has a movable actuator shaft arranged to move a teflon plunger located at one end of the gel syringe to cause gel material to quickly flow through a high pressure fitting at the other end of the gel syringe. Further, the gel delivery module uses the same components used in electrophoresis to relax the gel in the capillary tubes to achieve uniform gel distribution.

In another embodiment of the gel delivery module, a squeezable gel bag is utilized. In this embodiment, the gel bag is placed inside a high pressure chamber which includes a hollow cylinder with an open top and closed bottom and a cap removably affixed to the top of the cylinder. An outlet assembly including an inside end removably attached to the gel bag and an outside end connected to the T-fitting is affixed to the chamber. The chamber is also connected to a pressure control assembly capable of increasing or reducing the pressure inside the chamber. As the pressure increases inside the chamber, the gel is squeezed out through the outlet assembly and delivered to the T-fitting.

In another aspect of the preferred embodiment, a streamlined, off-line capillary reconditioner thoroughly cleans the capillary tubes off-line to achieve increased system throughput with a minimal increase in system cost. An operator can execute electrophoresis while cleaning a previously used capillary cartridge with the off-line capillary reconditioner. Since a thorough cleaning typically takes approximately twenty minutes, the off-line capillary reconditioner improves system throughput as the system does not have to wait for a thorough cleaning of the capillary cartridge 909 between consecutive executions of electrophoresis.

The off-line capillary reconditioner contains a small number of low-cost items including solvent containers for holding the cleaning fluids, manifolds for selection of the cleaning fluids and a simple controller for managing the cleaning. This streamlined nature of the off-line capillary reconditioner offers the advantage of increasing system throughput with a minimal increase in system cost.

BRIEF DESCRIPTION OF THE DRAWINGS

FIGS. 2A and 2B are a top and side view, respectively, of one embodiment of a cartridge of the present invention;

DETAILED DESCRIPTION OF THE PREFERRED EMBODIMENT

Figure 1:
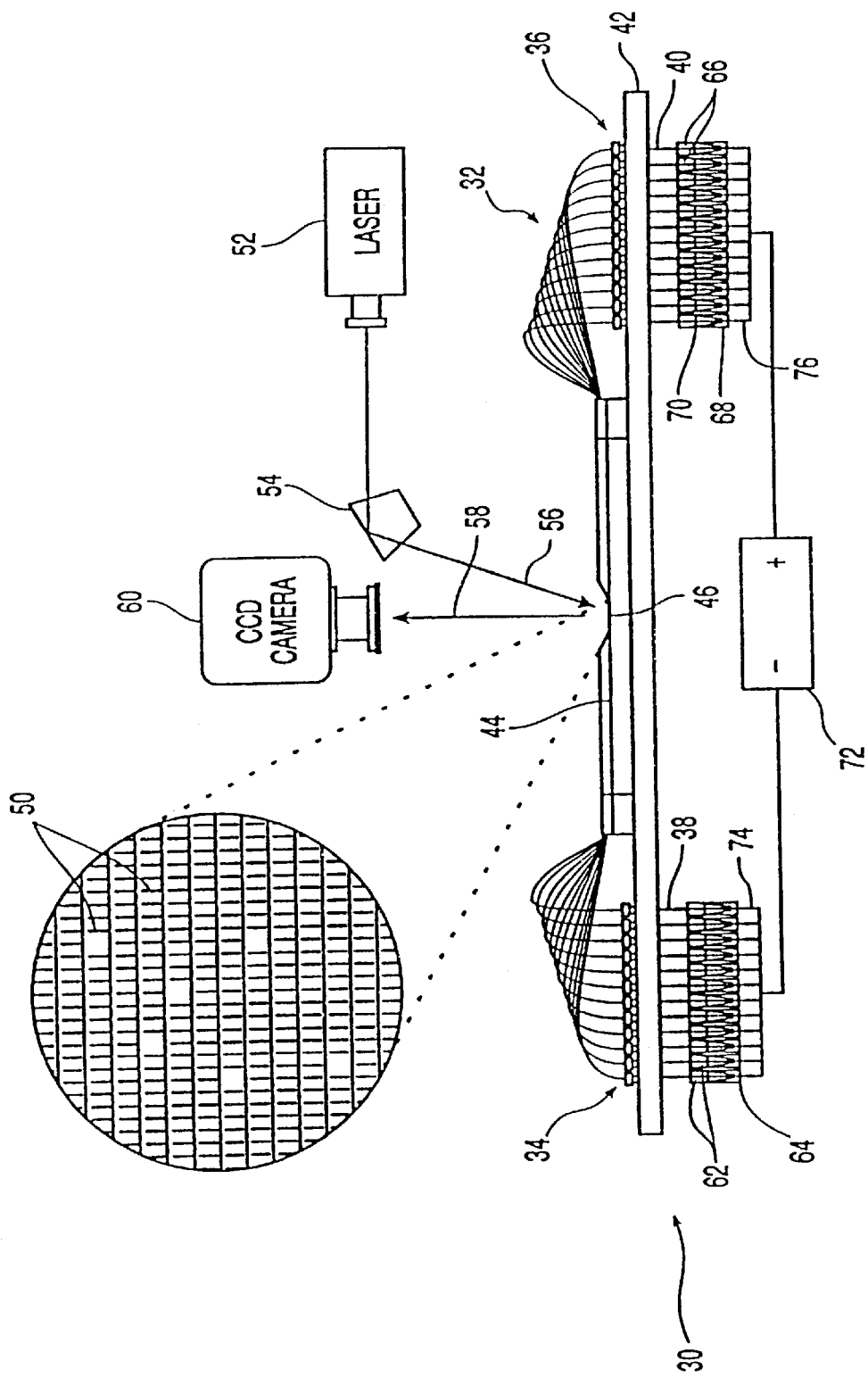
FIG. 1 is a side view of an arrangement in accordance with the present invention.

FIG. 1 presents a schematic illustrating the use of a device in accordance with the present invention. A cartridge 30 of the present invention comprises a plurality of capillary tubes 32 having substantially the same length. The capillary tubes extend between a sample-side connection array 34 and gel side connection array 36. The capillary tubes 32 terminate on the sample-side in an array of first capillary ends 38 and on the gel side in an array of second capillary ends 40.

Thus, both ends of each of the capillary tubes 32 in FIG. 1 extends through individual plate holes in a base member 42, which preferably is formed from polycarbonate, or acrylic or the like. Alternatively, each array of capillary ends may be retained in a separate mounting plate having the plate holes, and each of the mounting plates may then be fixed to a base member. Also, instead of passing each capillary tube through an individual plate hole, one or more capillary tubes may be collected together and sent through a common hole, or even no hole at all.

Between the two arrays, the capillary tubes 32 pass through a thermoelectric element 44 which is mounted on the base member 42. The thermoelectric element is arranged on either side of a window region 46. The thermoelectric element is used to control the temperature of the capillary tubes within a predetermined range. It should be evident to one skilled in the art that the thermoelectric element 42 may be comprised of two or more individual elements. It should also be evident that alternate temperature control means such as circulating fluid systems, and air convection may also be used to control the temperature.

The capillary tubes 32 are arranged parallel to one another, side by side, in the window region 46. The length of each capillary tube from its first capillary end to the window region 46 is substantially the same for all the capillary tubes 32. This length is determined by the optimization of (i.e., minimum acceptable) sample run time, and the minimum acceptable resolution of the separated samples. Nominally, this length in on the order of 50–70 cm. The window region 46 represents the region allowing access to the parallel capillary tubes from incoming excitation light. It also allows access to outgoing fluorescence emission from the capillary tubes. Thus, the window region 46 allows the bands 50 in the various capillary tubes to be detected.

As shown in FIG. 1, an excitation light source comprising a laser 52 and a prism 54 is used to focus a light beam 56 through the window region 46 and onto the capillary tubes 32. A fluoresced light beam 58 is then sensed by a CCD camera 60, which captures the bands 50. As is known to those skilled in the art, other illumination and detection means can also be used.

The arrangement of FIG. 1 provides for the substantially simultaneous introduction of samples into the array of first capillary ends 38 of all the capillary tubes 32. In particular, the arrangement allows one to introduce the various samples by simultaneously dipping the array of first capillary ends 38 into the wells 62 of a sample-side microtitre tray 64 having a standard size, as described above.

To allow for this, the individual capillary ends are spaced apart from one another such that they have a spatial arrangement which is substantially the same as, that of an array of wells belonging to a microtitre tray of standard size. Thus, the spacing between adjacent first capillary ends is approximately 0.9 cm and the entire array of first capillary ends has a footprint less than 7.5 cm×11 cm, thus corresponding to a microtitre tray of standard size.

The array of second capillary ends 40 is inserted into the wells 66 of a second microtitre tray 68, where they come into contact with a buffer solution 70, as known to those skilled in the art. As the wells 66 in the second tray 68 are separated from one another, the chance of cross-contamination among the second capillary ends 40 is reduced.

A voltage source 72 is used to provide a voltage differential between the two arrays of capillary ends. As shown in FIG. 1, one voltage level is applied through individual leads 74 to each of the wells 62 of the first microtitre tray 64 and a second voltage level is applied in substantially the same manner through leads 76 to the wells 66 of the second tray 68. Thus, current flows through the leads 74, into the individual samples, through the first capillary ends 38, through the capillary tubes 32, through the second capillary ends 40, into the buffer 70 present in the wells 66 of the second microtitre tray 68, and finally through leads 76.

FIGS. 2A and 2B shows a top and a side view of one embodiment of a cartridge 80 in accordance with the present invention. The cartridge has a base member 82 formed from polycarbonate, acrylic or the like. Mounted in the base member are first and second mounting plates 84, 86, respectively. Preferably, these plates are formed from an electrically insulative material.

An array of first capillary ends 88 project from the bottom surface 90 of the first mounting plate 84 and an array of second capillary ends 92 project from the bottom surface 94 of the second mounting plate. The capillary tubes 96 pass through, and are retained in, plate holes formed in the plates 84, 86 and project from the top surfaces 98, 100 of the plates. Preferably, each of the capillary tubes 96 is protected by a tube assembly 102 which is secured to a plate hole in the mounting plate, as it passes through the mounting plates.

As best seen in FIG. 2A, the tube assemblies, each with its associated capillary tubes, form a rectangular array of 8 rows and 12 columns as they emerge from the plates 84, 86. The spacing between adjacent plate holes in which the assemblies 102 are held, and the spacing of adjacent capillary ends 88, 92 correspond to the spacing of adjacent wells in a microtitre tray of standard size. In the preferred embodiment, adjacent capillary ends are separated by approximately 0.9 cm and the entire array of capillary ends, and thus the array of plate holes through which the capillary tubes 96 pass, form a footprint no larger than about 7.5 cm×11.0 cm.

The upper surface 98, 100 of each mounting plate 84, 86 is provided with first and second enclosures designated by reference numerals 104, 106, respectively. In the preferred embodiment, each of the enclosures is provided with an inlet 108 and an outlet 110. The outlet 110 of the first enclosure is connected to the inlet 108 of the second enclosure by plastic tubing 112. The inlet 108 of the first enclosure is connected to a first plastic shut off valve 114 while the outlet 110 of the second enclosure is connected to a second plastic shut off valve 116. The plastic shut off valves 114, 116 are connected, in turn, to respective first and second quick disconnects 118, 120.

During operation, the cartridge 80 can be connected to a pump assembly 122 which is arranged to circulate a temperature-controlled liquid coolant through the enclosures 104, 106. In such case, the cartridge's first disconnect 118 is connected to the output 124 of the pump assembly 122 while the second disconnect 120 is connected to the input 126 of the pump assembly 122. Such an arrangement maintains the temperature of those portions of the capillary tubes 96 projecting from the upper surfaces 98, 100 of the mounting plates and present in the enclosures 104, 106. For this to work, the mounting plates 84, 86 must form a liquid-tight seal with the base member 82. A liquid-tight seal must also be formed between the plate holes and the tube assemblies 102 and/or the capillary tubes 96 themselves.

The capillary tubes 96 pass between the two arrays of tube assemblies 102 in an area of the cartridge not covered by the enclosures 104, 106. As explained above, thermoelectric temperature control means 128, or the equivalent, is arranged on either side of a window region 130 of the capillary tubes 96 to control the temperature of the capillary tubes when they are no longer within the enclosures 104, 106.

Within at least a portion of the window region 130, the capillaries 96 are arranged parallel to one another so that they may be read by detection means. Preferably, the base member 82 is provided with an opening 132 above which the window region 130 is situated. This allows for at least one of illumination means or detection means to be placed below the base member from where they may be in a direct line of sight to the exposed capillary tubes 96.

Figure 3A:
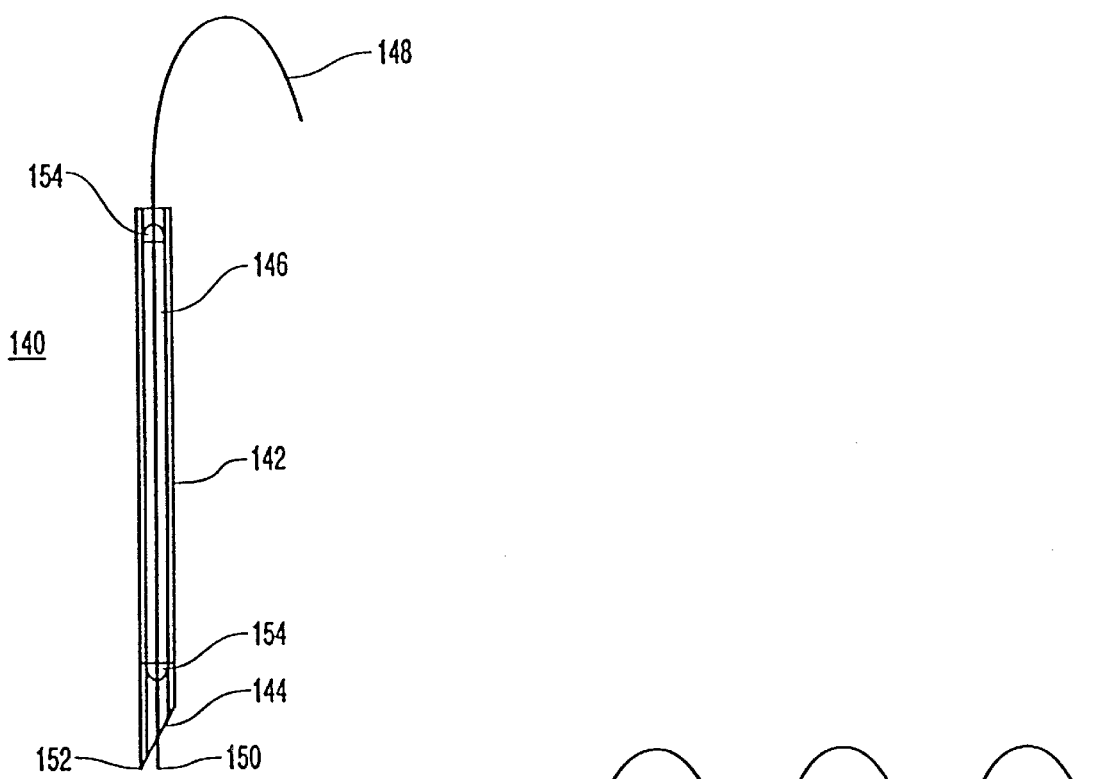
FIGS. 3A and 3B show a tube assembly and mounting arrangement for a cartridge of the present invention.
Figure 3B:
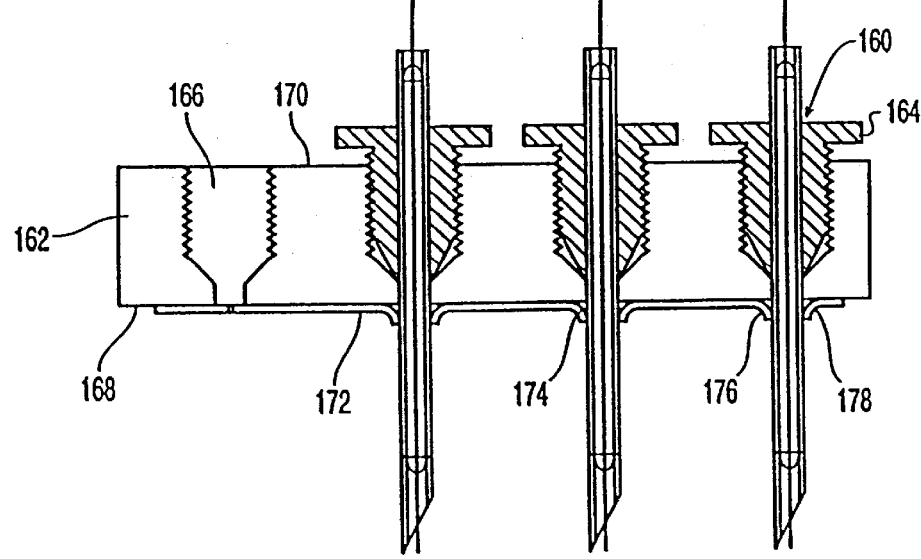

FIG. 3A shows a needle 140 used in forming a tube assembly 160 which can then be directly inserted into a mounting plate 162, as shown in FIG. 3B. The needle 140 comprises a metallic cannula 142. In the preferred embodiment, the cannula 142 is formed from stainless steel having an inner diameter of 0.064 in. and an outer diameter of 0.072 in. The cannula 142 is provided with a bevel 144 at the end which is dipped into a well.

Within the cannula 142 is a coaxially arranged annular polyetheretherketone (PEEK) polymer tubing 146 which serves as a sleeve. The polymer tubing 146 has an inner diameter of about 0.006 in. and an outer diameter of 0.0625 in. Thus, the polymer tubing 146 can be comfortably inserted into cannula Running through the center of the tubing 146, along a longitudinal axis of the needle 140, is a capillary tube 148 which is associated with the needle 140. The capillary tube 148 is formed from fused silica and has an inner diameter of about 0.003 in. and an outer diameter of about 0.006 in. Thus, the capillary tube 148 fits snugly into the polymer tubing 146. The capillary tube 148 terminates in an end 150 which is substantially across from the end 152 of the cannula 142. Thus, the spacing between the two ends 150, 152 is about 0.035 in.

An UV-cured, medical-grade epoxy sealant 154 is used at both ends of the polymer tubing 146 to secure it and the capillary tube 148 to the cannula 142. Preferably, the epoxy sealant 154 forms an air- and liquid-tight seal through the cannula 142. The epoxy sealant ensures that the polymer tubing 146 is not exposed to the environment, and also ensures that the capillary tube 148 does not come into direct contact with the cannula 142.

It should be noted that a needle may be formed in ways other than the one depicted in FIG. 3A. For instance, instead of a tubular cannula, the needle may simply comprise a capillary tube encased in a poured or coextruded plastic material which, in turn, is secured to a metallic strip. Other arrangements are also possible.

FIG. 3B shows a hollow, high pressure compression fitting 164 formed from nylon into which the needle 140 is inserted to complete the tube assembly 160. The needle 140 can be secured to the cylindrical inner walls of the compression fitting with an epoxy sealant. Each tube assembly 160 is then inserted into a plate hole 166 tapped in the mounting plate 162 and the plate hole 116, too, can be sealed with epoxy. When this is done, an air- and liquid-tight seal is provided between the bottom surface 168 and the top surface 170 of the mounting plate 162, allowing the mounting plate to withstand a positive pressure applied on its bottom surface in a region where the plate holes securing the tube assemblies are situated.

One may completely do away with the compression fittings 164 and drill plate holes in the mounting plate 162 which correspond in size to the outer diameter of the needles 140. In such case, a needle is directly inserted into each plate hole in the mounting plate 140 and secured thereto by the epoxy. Such a fitting-less approach can improve the structural integrity of the mounting plate 162 due to the reduced size of the plate holes. It may also provide a better air- and liquid-tight seal since there are fewer interfaces in which epoxy sealant is used. Moreover, it should also be understood that one may retain just a capillary tube 148, or just a capillary tube 148 encased in polymer tubing 146 directly in a plate hole of appropriate size formed in the mounting plate 162.

Whether or not one uses a compression fitting, and whether or not one uses a cannula and/or polymer tubing, it should be understood that in the preferred embodiment, each plate hole has one capillary tube retained therein. The array of plate holes preferably has a spatial arrangement corresponding to that of the wells of a microtitre tray of standard size. However, it may be possible to form the plate holes off-center, and then angle the capillary ends.

Furthermore, it should also be understood that it may be possible to fix an array of capillary ends in the desired configuration without forming holes in a mounting plate 162. For instance, this can be done by gluing or clamping the individual capillaries to a mounting plate so that their ends are arranged in the desired configuration. Alternatively, the capillaries may be secured together so that their ends remain in the desired configuration in a poured acrylic or the like. What is important is that the spacing of the capillary ends in the array correspond to the spacing of the wells in the microtitre tray of standard size.

A conductive plate 172 may be secured to the mounting plate 162 by screws, adhesives, or other conventional means. The conductive plate 172 is formed with an array of conductive holes 174 which corresponds to the plate holes 166 in the mounting plate. Each of the conductive holes 174 is formed by an H-shaped slit which forms a pair of tabs 176, 178 between the legs of the "H". When a needle 140 is inserted in the conductive hole 174, the tabs 176, 178 give way, and contact either side of the needle 140.

As the entire plate 172 is conductive, all needles 140 in the array share a common electrical connection. A voltage applied to the conductive plate 172 then appears on the exterior of each needle 140 in the array. During electrophoretic application, this voltage appears in the buffer solution found in each well, into which solution the capillary end 150 is inserted.

As is known to those skilled in the art, the voltage differential may be delivered to the first capillary ends through other means as well. For instance, instead of contacting a common plate to which the needles are connected, voltage leads may be connected directly to each needle. Alternatively, individual leads may be dipped into the liquid in each well. Another alternative is to deliver the voltage through a metallic coating, such as gold, deposited on the exterior of only the terminal portion of each capillary tube, where it contacts the liquid in the well. Also, the voltage may be delivered directly to the wells through one or more leads, as described earlier. One skilled in the art can readily formulate alternative approaches to delivering a voltage to the first capillary end.

Figure 4:
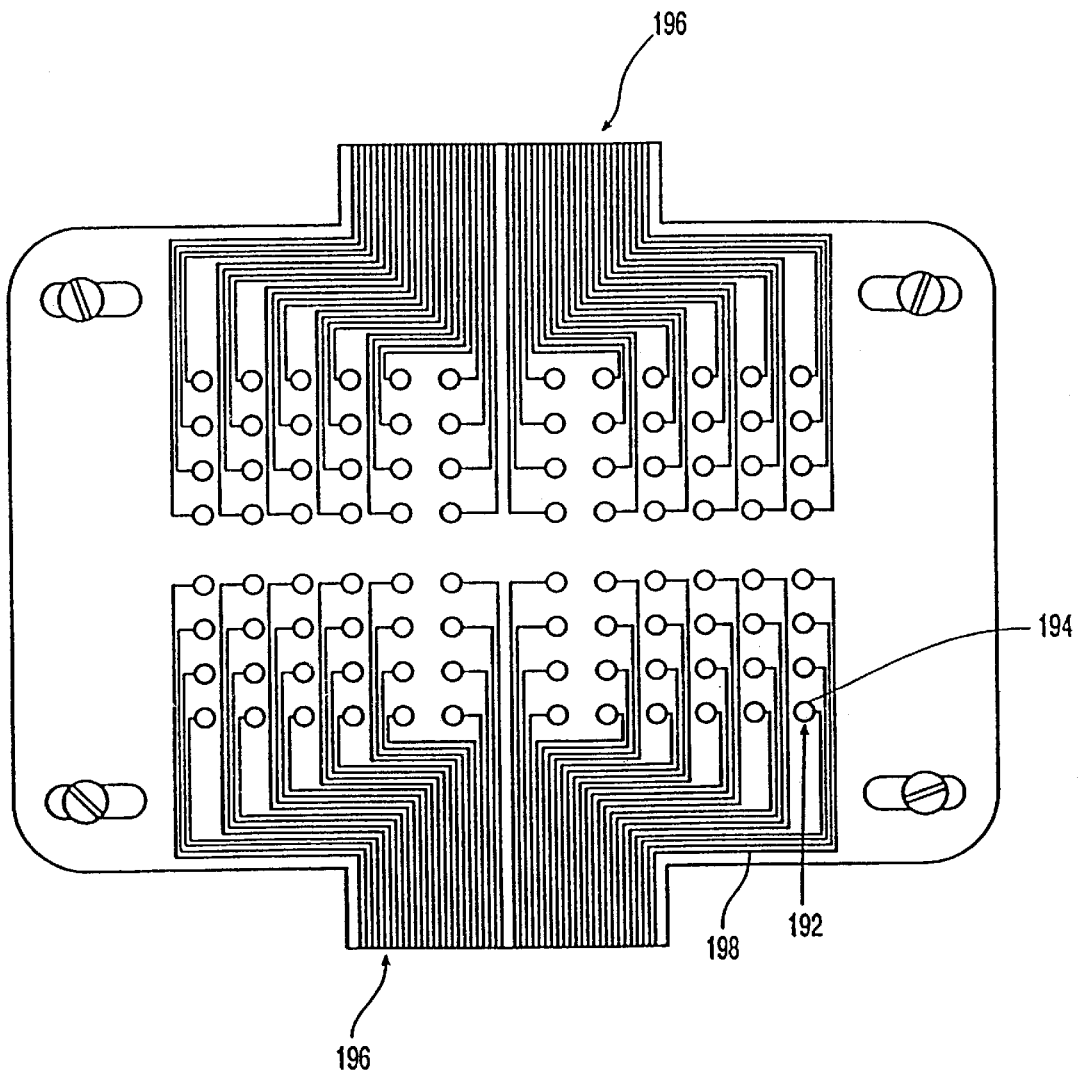
FIG. 4 shows a monitor plate which can be used with an array of needles.

FIG. 4 shows a monitor plate 190 which can be used with the cartridge embodiment shown in FIGS. 2A and 2B. In a cartridge of the present invention, the needles of at least the first mounting plate 84 are provided with a conductive plate 172 described above. The needles of the second mounting plate 86 can be provided with a monitor plate 190.

The monitor plate has an array of monitor holes 192. The array of monitor holes is aligned with the second array of plate holes formed in the second mounting plate 86. Each monitor hole 192 is formed with an isolated electrical contact 194 which is electrically connected to a monitor plate connector 196 by an individual lead 198. Each needle in the second mounting plate 86 contacts a corresponding electrical contact 194 in the monitor plate.

The purpose of the monitor plate is to provide a means for gauging the presence of electrical conductivity between any needle in the second mounting plate 86 and the needles of the first mounting plate 84. In this regard, it should be understood that the monitor plate 190 can be secured to mounting plate 86 in much the same manner as the conductive plate 172. What is important is that each of the electrical contacts 194 connects to only one needle in the second mounting plate.

Figure 5:
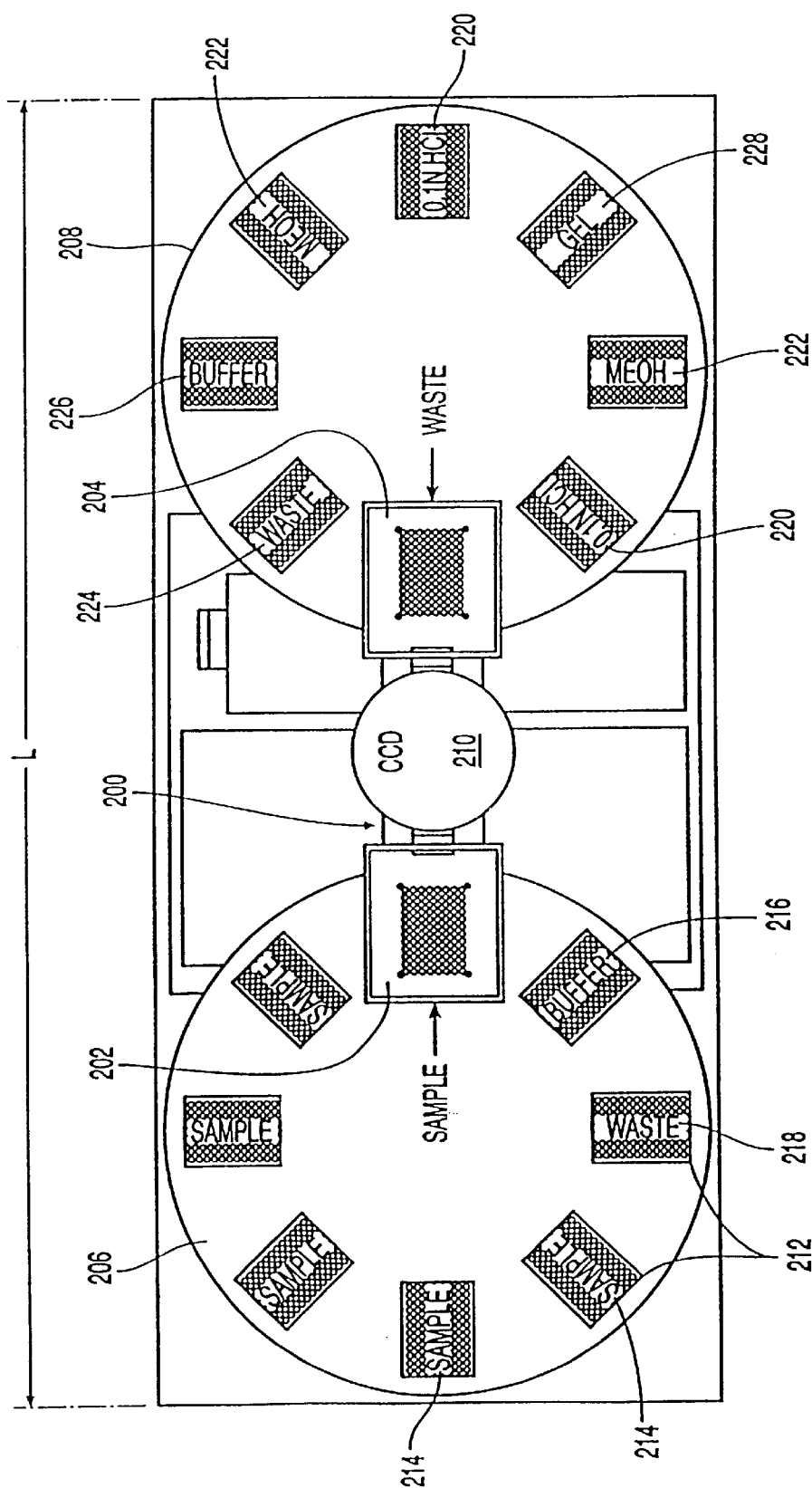
FIG. 5 shows the arrangement of an apparatus which can be used with the cartridge of FIGS. 2A & 2B.

FIG. 5 shows a cartridge 200 having a first 202 and a second 204 array of needles arranged above a first 206 and a second 208 carrousel, each array positioned above a portion of a respective carrousel. A CCD camera 210 is positioned above a portion of the cartridge between the two to detect bands in the capillary tubes (not shown in FIG. 5). Each carrousel 206, 208, has eight platforms 212, on each of which a microtitre tray having a standard size is placed.

The wells in each of these trays hold one or more liquids such as samples, gels, buffer solutions, acidic solutions, basic solutions, etc. As configured in FIG. 5, the first carrousel holds 6 sample trays 214, 1 buffer tray and 1 waste tray, a sample tray being positioned underneath the first needle array 202. As also shown in FIG. 5, the second carrousel holds a pair of acidic solution trays 220, a pair of basic solution trays 222, a pair of waste trays 224, one of which is positioned underneath the second needle array 204, a buffer solution tray 226, and a gel tray 228. Thus, the first carrousel 206 is the sample-side carrousel and the second carrousel 208 is the gel-side carrousel.

The cartridge is removably mounted to an automated electrophoretic apparatus. During operation, a lifting means raises and lowers the platform 212 which is under either of the two needle arrays 202, 204. When a microtitre tray is brought in close proximity to one of the needle arrays 202, 204, the needles in these arrays, and their associated capillary ends, are dipped into the contents of each well of that microtitre tray. When the platform under either of the needle arrays is lowered, the carrousel associated with that platform may be rotated so that a different platform 212 holding a different microtitre tray, can be raised.

When a platform is raised, surfaces around the periphery of the platform abut opposing surfaces, thus sealing a pressure chamber beneath the bottom surface of the needle array. Introducing a pressurized inert gas, such as helium, into the chamber at a pressure of 30 psi or so, applies a uniform force to the samples in the wells of the microtitre tray held on that platform. This causes a portion of each of samples to enter into the corresponding array of first capillary ends.

With, or in place of, applying pressurized helium to introduce samples into the first capillary ends, one may also apply a high voltage for brief period of time, on the order of 20–40 seconds, to cause the samples to migrate into the first capillary ends. Using a high voltage for this purpose, however, may be size-selective. That is, smaller molecules are more likely to enter the first capillary ends, potentially distorting the subsequent electrophoresis analysis.

The operation of the automated electrophoretic apparatus in accordance with FIG. 5 will now be described. First, the various microtitre trays are loaded with the designated buffer solutions, gels, samples, etc. Then, gel tray 228 in carrousel 208 is raised and gel is introduced into the capillary tubes (not shown in FIG. 5) through second capillary ends (hidden in FIG. 5) associated with the second needle array 204. The gel tray 228 is then lowered. A sample tray 214 in carrousel 206 is then raised, and sample is introduced through the first capillary ends (hidden in FIG. 5) associated with the first needle array 202. The sample tray 214 is then lowered. Carrousels 206 and 208 are then rotated to position buffer trays 216 and 226 under their respective needle arrays 202 and 204. A voltage differential is then applied across the two needle arrays to perform the electrophoresis run.

Upon completion of the run, the cartridge may be reconditioned. This is done by flushing out the gel and samples from the previous run under pressure and cleaning the capillary tubes using the acidic 220 and/or basic 222 solutions. The cartridge is then ready for re-use, allowing the samples in another one of the sample trays 214 to be tested.

It should be obvious that the carrousels 204, 206 may be formed with a different number of platforms. It should also be obvious that one can use a linear, or rectangular, or other arrangement of such platforms. All that is required is a storage and positioning system which allows a first particular microtitre tray to be brought to the first needle array 206, and a second particular microtitre tray to be brought under the second needle array 208.

Figure 6A:
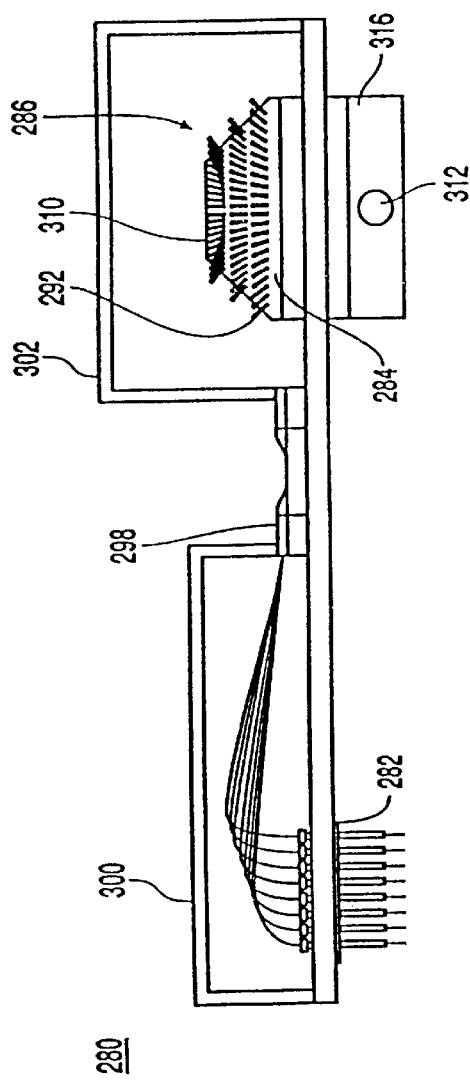
FIGS. 6A and 6B are a side and a top view, respectively, of a second embodiment of a cartridge of the present invention.
Figure 6B:
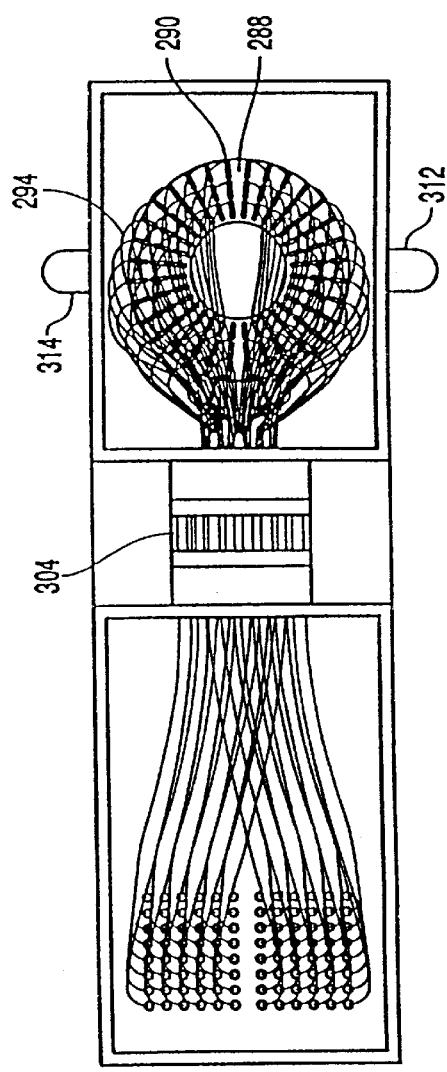

FIGS. 6A and 6B present a side and a top view, respectively, of a cartridge 280 having a first mounting plate 282 in which the array of plate holes in the first mounting plate 282 is rotated by 90°. Otherwise, the arrangement for connecting the capillary tubes to the first mounting plate is substantially the same as previously described. The first capillary ends formed in an array with the desired spacing project from the bottom surface of the first mounting plate 282, and are retained in plate holes formed in the first mounting plate.

The second mounting plate 284, however, is not the same as in the previous cartridge embodiment. In the cartridge 280, the second mounting plate 282 serves as a pressure containment member of a pressure cell 286 having substantially cylindrical exterior walls. For the sake of clarity, FIG. 6A does not show all the capillary tubes on the first mounting plate, nor any capillary tubes at all on the second mounting plate 284. It is to be understood, however, that all the capillary tubes are present.

The second mounting plate has a radially symmetric, beveled surface 288 in which a plurality of plate holes 290 are formed. Each of these plate holes 290 is fitted with a section of PEEK polymer tubing 292 in which the capillaries are encased using an UV-cured epoxy, as described before, to form an air- and liquid-tight seal in the plate holes 290. The capillary tubes pass through the PEEK polymer tubing and a second end of each capillary tube communicates with an interior cavity of the pressure cell. Although the preferred embodiment for this cartridge uses just PEEK polymer tubing and a capillary tube in the second mounting plate, it should be understood, that needles similar to the ones described earlier, could also be used. Also, just the capillary tubes alone, secured by epoxy, can be used as well. What is important is that each capillary tube 294 is retained in a plate hole 290 in an air- and liquid-tight manner, and that the capillary tube's second end communicates with an interior cavity of the pressure cell 286.

As is the case with cartridge 80 of FIGS. 2A and 2B, this cartridge 280 is provided with thermoelectric control means 298, enclosures 300, 302, and its capillary tubes are arranged in parallel along at least a portion of a window region 304. Although not shown in FIGS. 6A and 6B, it is understood that the enclosures 300, 302 can be provided with inlets and outlets and the like for circulating a coolant, as was the case with the other cartridge 80.

As shown in FIG. 6A, the second mounting plate 284 has a truncated cone-shaped upper portion terminating in a flat top 310. The curved, conical surface 288 in which the plate holes 290 are formed, is advantageous for reasons of structural integrity when a high positive pressure is applied from underneath the second mounting plate. Also, placing the plate holes 290 on such a surface allows them to be placed farther apart, a feature which also enhances the structural integrity of the pressure cell 286.

The pressure cell 286 is secured to the base member of the cartridge 280 and projects through the bottom of the base member. This arrangement allows the pressure cell 286 to be provided with an inlet 312 and an outlet 314 arranged on opposite sides of its cylindrical exterior walls. It should be noted that the inlet could just as easily be formed in the flat top portion 310 of the second plate 284, and the outlet formed in the bottom surface of a lower portion 316 of the pressure cell 286. In such case, the pressure cell could be rest on the base member, rather than project through its bottom, with a pipe fitting connected to the outlet through a hole formed in the base member, which hole is then sealed.

Figure 7:
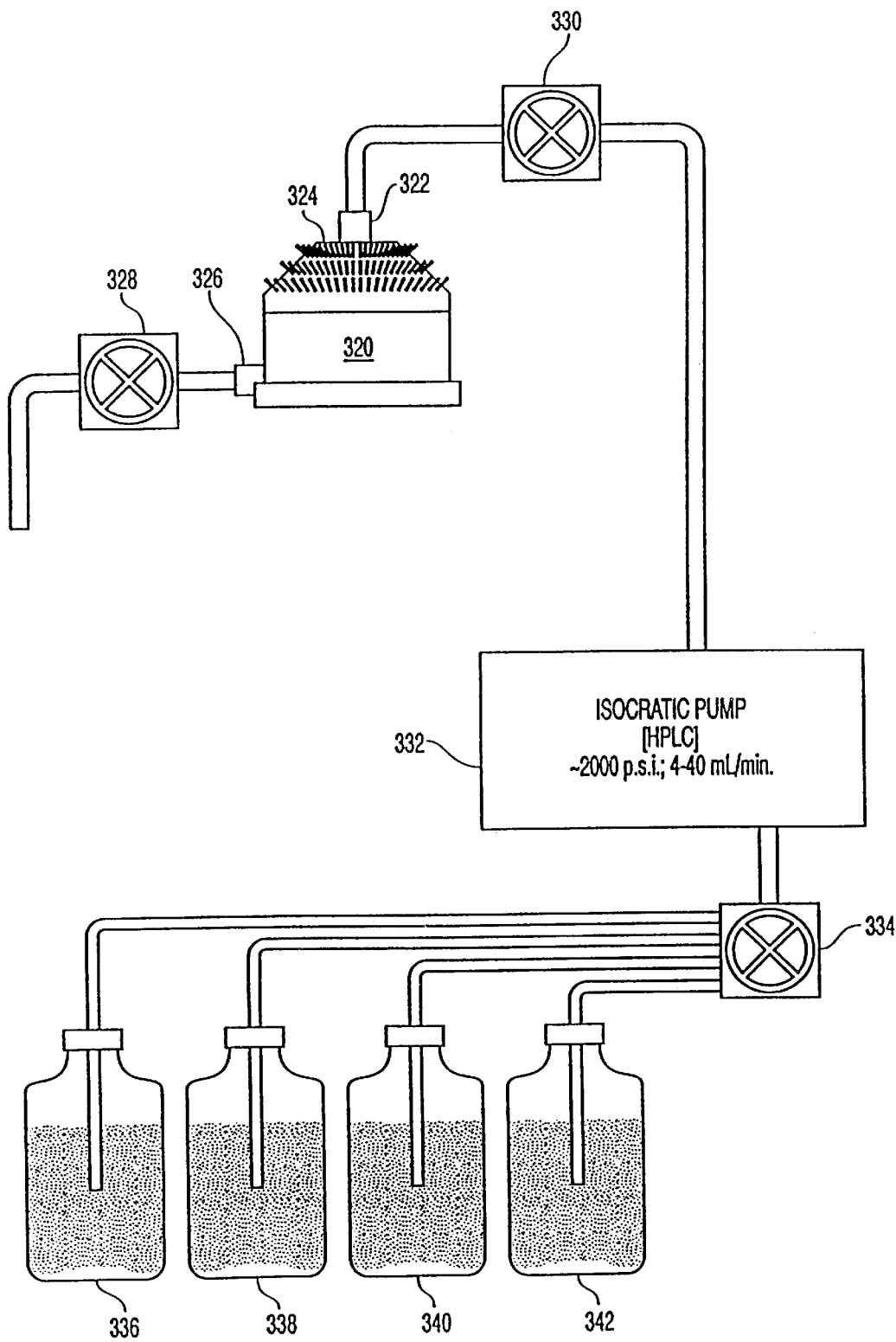
FIG. 7 shows the valving arrangement for a pressure cell similar to the one shown in the cartridge of FIGS. 6A and 6B.

FIG. 7 shows a valving arrangement for a pressure cell 320 which has an inlet 322 at its top surface 324, but otherwise is substantially similar to the pressure cell 286. Aside from the inlet 322, the pressure cell 320 is also provided with an outlet 326, which is connected to a waste valve 328. The waste valve 328 is opened to expel the contents of an interior cavity of the pressure cell 320.

Access to the inlet is 322 controlled by a shut-off valve 330. Liquids can be passed through the inlet 322 into the pressure cell 320 with the use of a pump 332. Preferably, the pump is a high pressure liquid chromatography (HPLC) pump having a pumping capacity of 4–40 milliliters per minute, at a pressure of about 2000 psi. The pump 332 is connected to a multi-valve manifold 334 which selectively allows one of four liquids to be pumped into the pressure cell. The four liquids are held in separate containers 336, 338, 340, 342, which respectively hold gel, a buffer solution, an acidic solution, and a basic solution. Additional containers holding the same liquids may be held in reserve, or connected in series with these, so as to increase the total supply.

The waste valve 328, the shut-off valve 330, the pump 332 and the multi-valve manifold 334 are all under the direction of a controller, preferably a microcomputer, or equivalent.

Thus, the contents of an interior cavity of the pressure cell are regulated by the controller. Such a controller may also receive inputs from various pressure and temperature monitors and other sensors to prevent damage to the pressure cell 320.

During operation, the interior cavity of the pressure cell 320 is filled by means of the pump 332. This forces the pumped liquid into the second capillary ends which communicate with the interior cavity of the pressure cell 320. By filling the array of first capillary ends and the pressure cell 320 with the appropriate fluids in the appropriate sequence, one may perform the electrophoresis operations, much as described above with regard to the apparatus of FIG. 5.

After the run, one may recondition the pressure cell and the capillary tubes to prepare them for another run. Again, this is accomplished by flushing the gel and sample from all the capillary tubes simultaneously. With the pressure cell 320, however, pressures on the order of several thousand psi can be applied. These increased pressures force the viscous gel out of the capillary tubes much faster. This reduces the cycle time between runs, with reconditioning, to about one to two hours.

Figure 8:
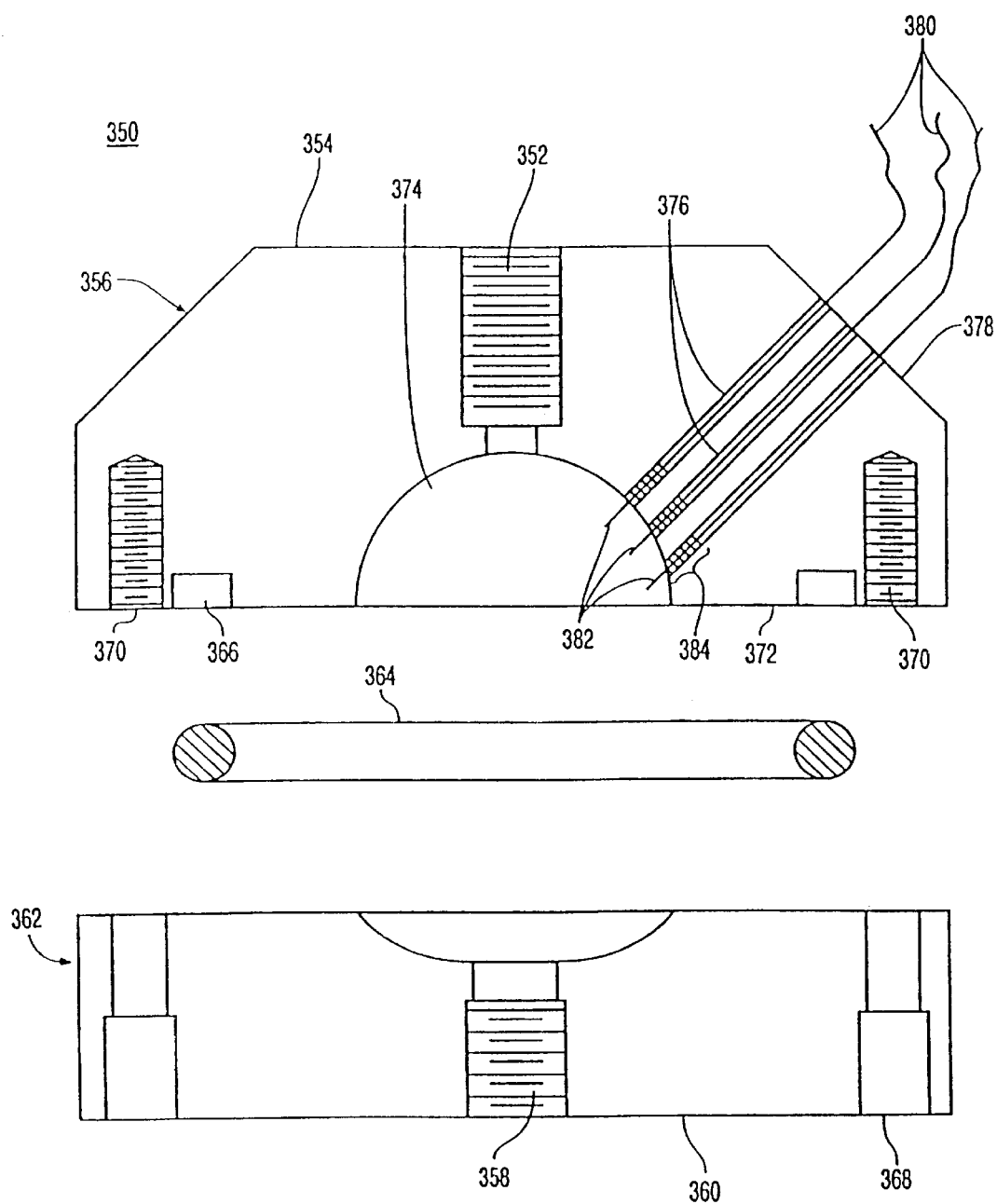
FIG. 8 shows an exploded view of a pressure cell vertical cross-section.

FIG. 8 shows an exploded cross-section of a pressure cell 350, similar to the pressure cell 286 in the cartridge 280. As is the case with the other pressure cells, pressure cell 350 is preferably formed from aluminum or stainless steel. The pressure cell 350 is provided with a threaded inlet 352 formed on the top surface 354 of its upper portion 356, which upper portion comprises the second mounting plate. The pressure cell 350 is also provided with a threaded outlet 358 on the bottom surface 360 of its lower portion 362. High pressure pipe fittings can be screwed into the threads of the inlet 352 and the outlet 358.

The upper portion 356 and the lower portion 362 are held together by a plurality of bolts (not shown) which are inserted through bolt holes 368 formed along the periphery of the bottom surface 360 of the lower portion 362. The bolts are then screwed into corresponding threaded holes 370 formed on the bottom surface 372 of the upper portion 356. An O-ring 364 partially fits into a rectangular channel 366 formed in the second mounting plate 356. The O-ring 364 provides a seal between the upper portion 356 and the lower portion 362. Instead of an O-ring, a gasket, or the like may be used to effect such a seal.

At the center of the pressure cell 350, formed between the upper 356 and lower 362 portions is an interior cavity 374. A plurality of plate holes 376 are formed in the upper portion (second mounting plate). For simplicity, in FIG. 8, the plate holes 376 are only shown on one side of the upper portion 356. It should be understood, however, that they are also present on the other side. The plate holes 376 extend from a beveled surface 378 formed on the upper portion 356 to the interior cavity 374.

Capillary tubes 380 are retained in these plate holes 376 and their second ends 382 communicate with the interior cavity 374. Preferably, each capillary is encased in a section of PEEK polymer tubing which extends from a point within each plate hole 376, proximate to the interior cavity 374, to well outside the beveled surface 378. For simplicity, however, the PEEK tubing is not shown in FIG. 8. Nevertheless, it should be kept in mind that just the capillary tube, or a needle comprising a capillary tube, PEEK tubing and a cannula, can be inserted into each plate hole 376, assuming that it is suitably sized.

As explained above, an UV-cured epoxy sealant is used to seal the plate holes 376 at both ends so that they are air-and liquid-tight. With the pressure cell, the terminal portion 384 of each plate hole proximate to the interior cavity 374 is tapped or roughened. This provides a surface to which the epoxy sealant bonds more readily during assembly.

A liquid held within the interior cavity 374 is in contact with the material forming the interior cavity. When the liquid is also in contact with the second capillary end 382, an electrical connection between the interior cavity 374 of the pressure cell 350 and the first capillary end secured to the first mounting plate, is completed. Thus, grounding the pressure cell 350 through a contact formed thereon, applies the ground to the interior cavity 374, completing the circuit necessary to perform the electrophoresis. Alternatively, as the pressure cell 350 is electrically isolated from the base member to which it is mounted, the potential of the pressure cell 350 may be allowed to float. This allows one to apply a high voltage to the pressure cell 350, rather than to the needles associated with the first capillary ends.

Figure 9:
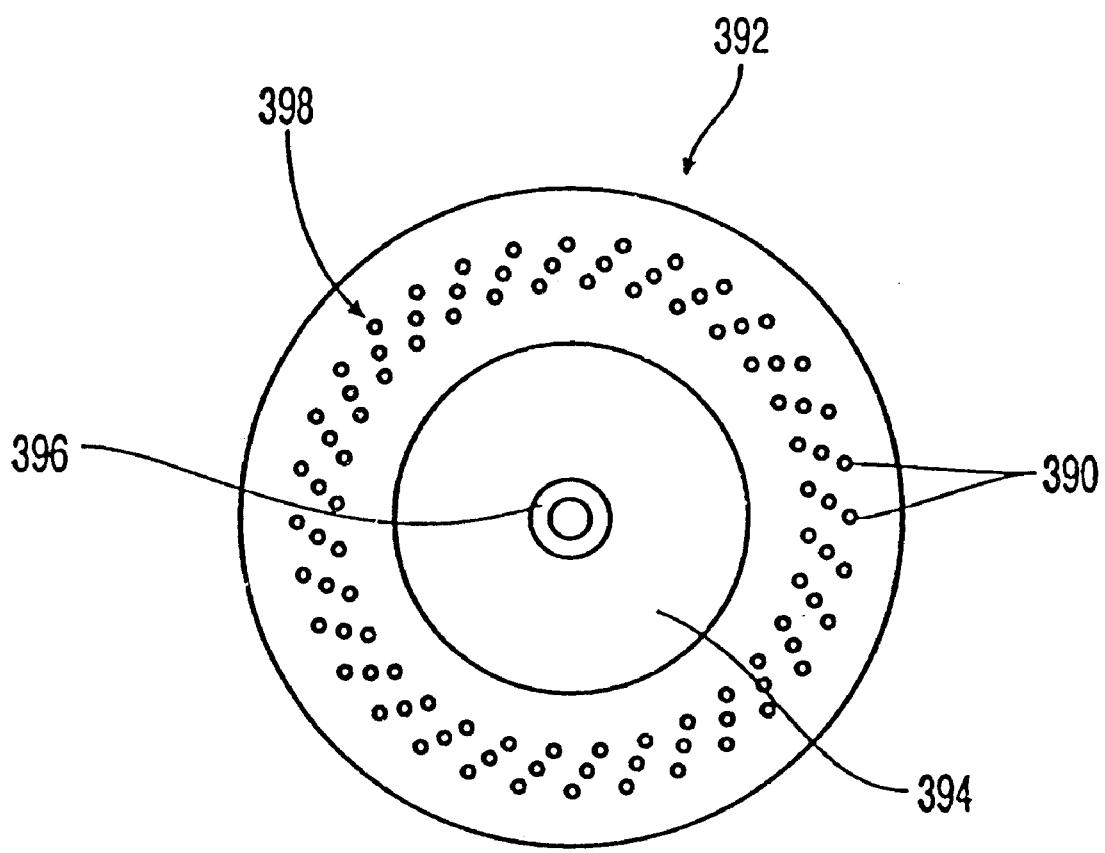
FIG. 9 shows a top view of a second mounting plate of a pressure cell having an alternate arrangement of plate holes.

FIG. 9 shows an alternate arrangement for the plate holes 390 in a second mounting plate 392 having a top surface 394 and an inlet 396. In this arrangement, each set 398 of three plate holes is offset at an angle relative to the center of the top surface 394. This provides for a maximum spacing between the plate holes. From a structural integrity point of view, such an arrangement may be preferable to having the plate holes arranged radially, in a spoke-like fashion, as shown in FIG. 6B.

Figure 10:
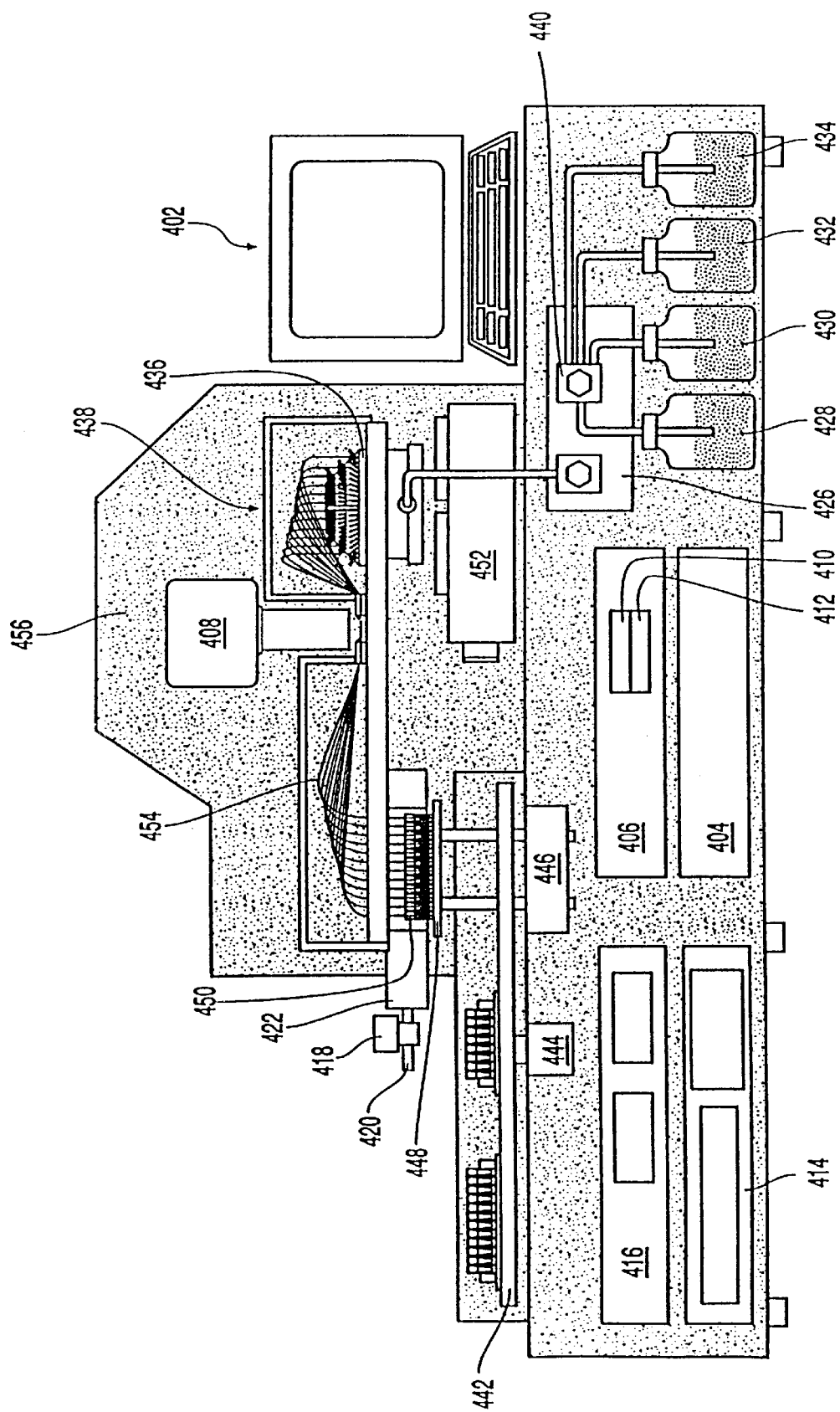
FIG. 10 shows an electrophoretic apparatus in accordance with the present invention.

FIG. 10 shows an electrophoretic apparatus 400 designed for use with a capillary cartridge formed in accordance with FIGS. 6–9. The apparatus comprises a user interface 402, shown as a video display terminal and keyboard, which communicates with a controller 404, which preferably is a microprocessor-based computer, or the like. The user interface 402 allows a user to enter commands, receive status information, and view the collected data.

The apparatus 400 also comprises a data processing computer 406, which receives, stores and processes video signals from a CCD camera 408. The data processing computer 406 is provided with optical 410 and/or magnetic 412 read/write data storage means. Resident in the data processing computer 406 are signal and image processing software to analyze the signal data from the camera 400. The data processing computer 406 is connected to the controller 404, and responds to requests from the latter, exchanging data and control information, as needed.

The apparatus 400 is further provided with a high-voltage power supply 414 which provides the necessary voltage to be applied across the ends of the capillary tubes. The power supply's operation is directed by the controller 404.

The controller 404 also directs the operation of a pump interface 416, which comprises a number of electronic switches. The pump interface 416 regulates the operation of a solenoid valve 418. The solenoid valve 418 connects a gas inlet 420 which is connected to an inert gas source, such as a pressurized helium tank, to the chamber 422. The pump interface 416 also regulates the operation of high pressure liquid chromatography (HPLC) pump 426. The HPLC pump 426, under the direction of the controller, selectively supplies liquids in containers 428, 430, 432, 434, gel, buffer solution, an acid, and a base, to a pressure cell 436 of a cartridge 438 through a multi-valve manifold 440.

A carrousel 442 having a plurality of platforms 448 is turned by a rotor 444. A lifting means 446, such as a hydraulic pump or the like, raises and lowers a platform 448 positioned under a first mounting plate. This brings a microtitre tray 450 on the platform 448 towards and away from an array of capillary ends, as previously described. Both the rotor 444 and the lifting means are connected to, and driven by, the controller 404.

The apparatus 400 also includes a light source 452, preferably a laser, which illuminates the capillary tubes 454, as directed by the controller 404. The light source 452 illuminates the capillary tubes 454 from below, through an opening in a base member of the cartridge 438, as previously described. A light shroud 456 covers the camera 408, the light source 452, and at least the window region of the capillary tubes 454, as the detection of the capillary bands is performed in the dark.

During operation, the capillary tubes 454 are first cleaned and then loaded with gel through the pressure cell 436 by activating pump 452. The pump 452 is then turned off. Next, a platform 448 carrying a microtitre tray 450 holding samples is raised by the lifting means 446. This forms a seal between the platform 448 and the underside of the chamber 422. It also dips the first capillary ends into the wells of the microtitre tray 450. With the chamber 422 sealed, the solenoid valve 418 is opened, allowing pressurized helium gas to enter through the inlet 420. This puts a uniform positive pressure on the samples in each of wells of the microtitre tray 450, on the order of 30 psi, and forces the samples at least slightly into the first capillary ends. As discussed above, a high voltage may be applied for a brief period of time for this purpose, as well. The platform 448 is lowered and the carrousel 442 is rotated, bringing a microtitre tray filled with buffer solution under the first capillary ends. Next, the buffer tray is raised so that the first capillary ends are dipped into the buffer solution, and the pressure cell 436 is filled with buffer solution so that the second capillary ends are in contact with buffer solution, as well. After this, the high voltage source 414 is turned on to perform the electrophoresis run. The light source 452 and the camera 408 are used to simultaneously detect the bands in all the capillary tubes 454. The video signal data from the camera 408 are processed and stored in the computer 406. The processed data may then be presented on the user interface 402. After the run, the cartridge 438 may be reconditioned (i.e., cleaned) and prepared for another run.

The carrousel arrangement shown in FIG. 5 has a buffer contamination problem. As shown in FIG. 5, there are 6 sample trays 214 and one buffer tray 216 on the first carrousel 206. After a sample has been introduced from a sample tray 214 on the first carrousel 206 through the first capillary ends (hidden in FIG. 5), the sample tray 214 is lowered, carrousels 206 and 207 are rotated to position buffer trays 216 and 226 under their respective needle arrays 202 and 204, and a voltage differential is applied across the two needle arrays 202, 204 to perform electrophoresis. While the first capillary ends (hidden in FIG. 5) are in contact with the buffer tray 216, some of the DNA sample from the first capillary ends will diffuse into the buffer tray 216 and thereby contaminate the buffer tray 216. This contamination will adversely effect the accuracy of a subsequent electrophoresis run with a DNA sample from another sample tray 214 because this subsequent electrophoresis run will use the same buffer tray 216 as the previous run.

This contamination problem could be eliminated by replacing sample trays 214 with buffer trays 216 until there is a one to one correspondence between the set of sample trays 214 and the set of buffer trays 216 on the first carrousel 206. With this arrangement, each sample tray 214 has a single, corresponding buffer tray 216. While this arrangement eliminates the contamination problem, it adversely effects the capacity of the first carrousel 206. If the first carrousel 206 has eight platforms, the first carrousel 206 can only have a maximum of three sample trays 214 in order to achieve the one to one correspondence between the set of sample trays 214 and the set of buffer trays 216, necessary to eliminate the contamination problem.

Figure 11:
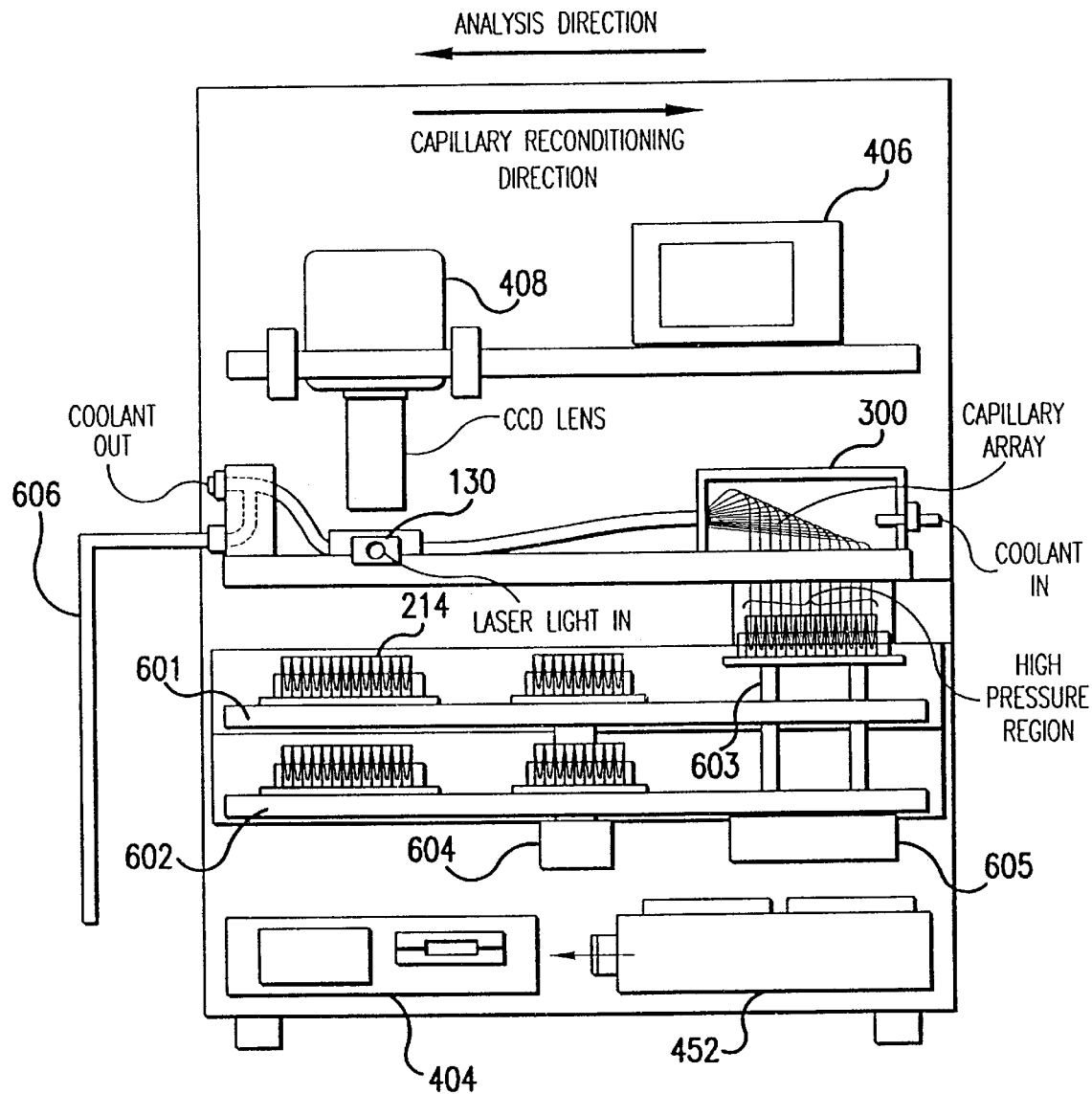
FIG. 11 shows a sequencer module which includes the stacked, dual carrousel arrangement.

FIG. 11 illustrates a stacked, dual carrousel arrangement in a sequencer module 600 which achieves a one to one correspondence between the sample trays 214 and buffer trays 216 to eliminate the contamination problem, without reducing the capacity of the system. The stacked, dual carrousel arrangement has an upper carrousel 601 and a lower carrousel 602 which are aligned and spaced apart along a common axis.

In the preferred embodiment, both carrousels 601, 602 have seven sites 618 for accommodating microtitre trays 214, 216 and one large cut-out 620 for enabling passage of microtitre trays 214, 216. The large cut-out 620 on the upper carrousel 601 allows passage of a tray initially positioned on a site 618 of the lower carrousel 602 through the upper carrousel 601 to the needle array 603.

Figure 12A:
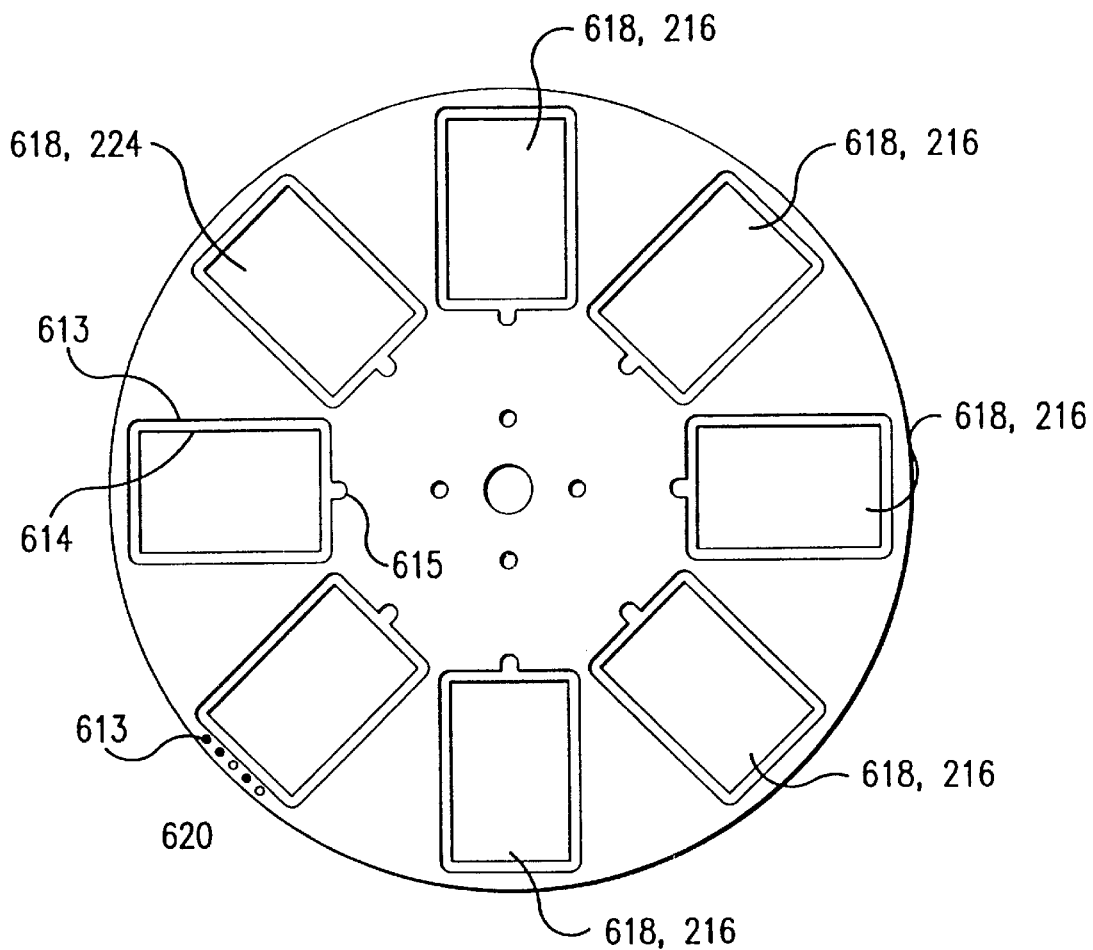
FIG. 12 shows a detailed view of a carrousel contained in the stacked, dual carrousel arrangement.

In one embodiment, the upper carrousel 601 holds the sample trays 214 and the lower carrousel 602 holds the buffer trays 216 corresponding to the sample trays 214. FIG. 12A shows this tray arrangement on the lower carrousel 602. With this tray arrangement, the lower carrousel 602 could hold six buffer trays 216 and a waste tray 224. The upper carrousel 601 could hold six sample trays 214. In the preferred embodiment, each carrousel includes six sample trays, six buffer trays, one drain tray, and one water tray. The water tray is provided for rinsing the first ends of capillaries and electrodes. However, the number of each type of trays placed on a carrousel varies as the size of commercially available microtitre trays changes.

Each of the carrousels 601, 602 in the stacked, dual carrousel arrangement contains a rotor 604 and a motor 608 for selectively rotating the carrousels 601, 602 to a chosen angular position. Specifically, the motor 608 selectively rotates the carrousels 601, 602 to position the appropriate site 618 accommodating a sample tray 214, buffer tray 216 or waste tray 224 under the needle array 603. A controller 404 causes the motor 608 to selectively rotate each carrousel 601, 602 to a chosen angular position.

In the preferred embodiment, the stacked, dual carrousel arrangement has a motor 608 for each carrousel 601, 602. The motor 608 is a stepper motor, available from Pacific Scientific in Wilmington, Mass. In another embodiment, the stacked, dual carrousel arrangement has a DC motor 608 and a clutching mechanism for selectively engaging and rotating each carrousel 601, 602.

The angular position of the two carrousels are automatically detected. For this, each carrousel 601, 602 also has an encoder 612 which is operatively engaged to the rotor 604. The encoder 612 senses angular position data of the rotor 604 and sends this data to the controller 404. In the preferred embodiment, the encoder 612, available from Stegmann Corporation in Vandalia, Ohio (Model Number AG612XKRR, 2048) has an optical sensor and has a 2048 pulse resolution value.

The angular position can also be detected by means of a linear arrangement of holes 613 placed along the periphery of the carrousel, adjacent each site. For a carrousel with 8 sites, a leading hole, three coding holes, a trailing hole are provided. The leading and trailing holes simply serve to indicate that coded holes maybe present there between. The three coding holes may each be present, or absent. This allows one to code for 8=2×2×2 sites. The holes are illuminated by LEDs located above the upper carrousel 601; the LED light passes through the holes and is detected by a carrousel location detector located below the lower carrousel 602. The carrousel location detector generates the angular position data from the sequence of holes through which LED is visible light and sends this data to the controller 404.

The controller 404 determines the rotational position of each carrousel 601, 602 using the angular position data from either of the above embodiments to cause the motor 608 to selectively rotate each carrousel 601, 602 to a chosen angular position. Specifically, the controller 404 uses the position data to compensate for the rotational momentum of the carrousel 601, 602 which can cause the carrousel 601, 602 to initially go beyond its chosen angular position.

The stacked, dual carrousel arrangement also contains a DC motor 605 having a movable member to move the chosen tray 214, 216, 224 along the common axis toward or away from the needle array 603 as needed. The controller 404 causes the motor 605 to move the chosen tray 214, 216, 224 along the common axis.

The motor 605 also contains a current meter to measure the current drawn by the DC motor 605. When a DC motor encounters a load, the current drawn by the motor increases to permit continued movement of its movable member. Accordingly, the current increases sharply when a tray 214, 216, 224 reaches the needle array 603 while traveling upward or when a tray 214, 216, 224 reaches a carrousel 601, 602 while traveling downward. Upon detecting a sharp increase in the current, the controller 404 causes the DC motor 605 to stop as the tray 214, 216, 224 has reached its proper position.

Figure 12B:
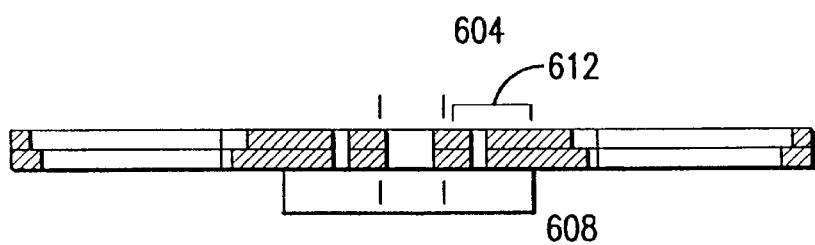

In the preferred embodiment as shown in FIG. 12A and FIG. 12B, the diameter and thickness of each carrousel 601, 602 are 23.5 inches and 3/8 inches respectively. Further, each carrousel 601, 602 has a circular hole 610 in its center with a diameter of 1.375 inches to receive a rotor 604. Each carrousel 601, 602 has four holes 611 with a diameter of 5/16 inches equally spaced along the periphery of a circle centered at the center of the carrousel 601, 602 with a diameter of four inches. The carrousels 601, 602 are bolted to a bearing assembly which is fixed on an axle through these four holes 611 in order to balance the carrousels 601, 602 on the bearing assembly to enable their controlled rotation.

In the preferred embodiment, two rectangular openings 613, 614 form the sites 618 on each carrousel 601, 602. The size of the opening on the top side 613 of the carrousel 601, 602 is slightly larger than size of the trays 214, 216, 224. An exemplary length and width of the top opening 613 are 5.95 inches and 4.187 inches respectively. The size of the opening on the bottom side 614 of the carrousel 601, 602 is slightly smaller than the size of the trays 214, 216, 224. The slightly smaller size of the bottom opening 614 allows a lip of a tray 214, 216, 224 to rest on the site 618. An exemplary length and width of the bottom opening 614 are 5.45 inches and 3.687 inches respectively. Each site 618 on each carrousel 601, 602 also has a recess 615 which matches a tab on the trays 214, 216, 224 to ensure its proper orientation.

In the preferred embodiment, the cut-out 620 is an opening which is entirely bounded by the carrousel 601, 602. In this embodiment, the movable member of the motor 605 must move within the periphery of the carrousel 601, 602 to avoid hitting the carrousel 601, 602 since the opening is entirely bounded by the carrousel 601, 602.

In an alternate embodiment, the cut-out 620 is partially bounded by the carrousel 601, 602 and is unbounded along the periphery of the carrousel 601, 602. In this embodiment, the movable member of the motor 605 does not need to move within the periphery of the carrousel 601, 602 to avoid hitting the carrousel 601, 602 since the cut-out 620 is unbounded along the periphery of the carrousel 601, 602. Accordingly, the movable member of the motor 605 can move outside the periphery of the carrousel 601, 602 in this embodiment.

The sequencer module 600 (FIG. 11) also contains elements discussed previously which work in conjunction with the stacked, dual carrousel arrangement to perform electrophoresis. These elements include a CCD camera 408, a laser 452, a high pressure chamber 422, an array of capillary tubes 454, an optical window region 130, and an enclosure forming a coolant region 300. The solvent/gel delivery module 800 described subsequently in FIGS. 14A–C delivers solvent or gel to the sequencer module 600 through the solvent/gel input port 606.

Figure 13:
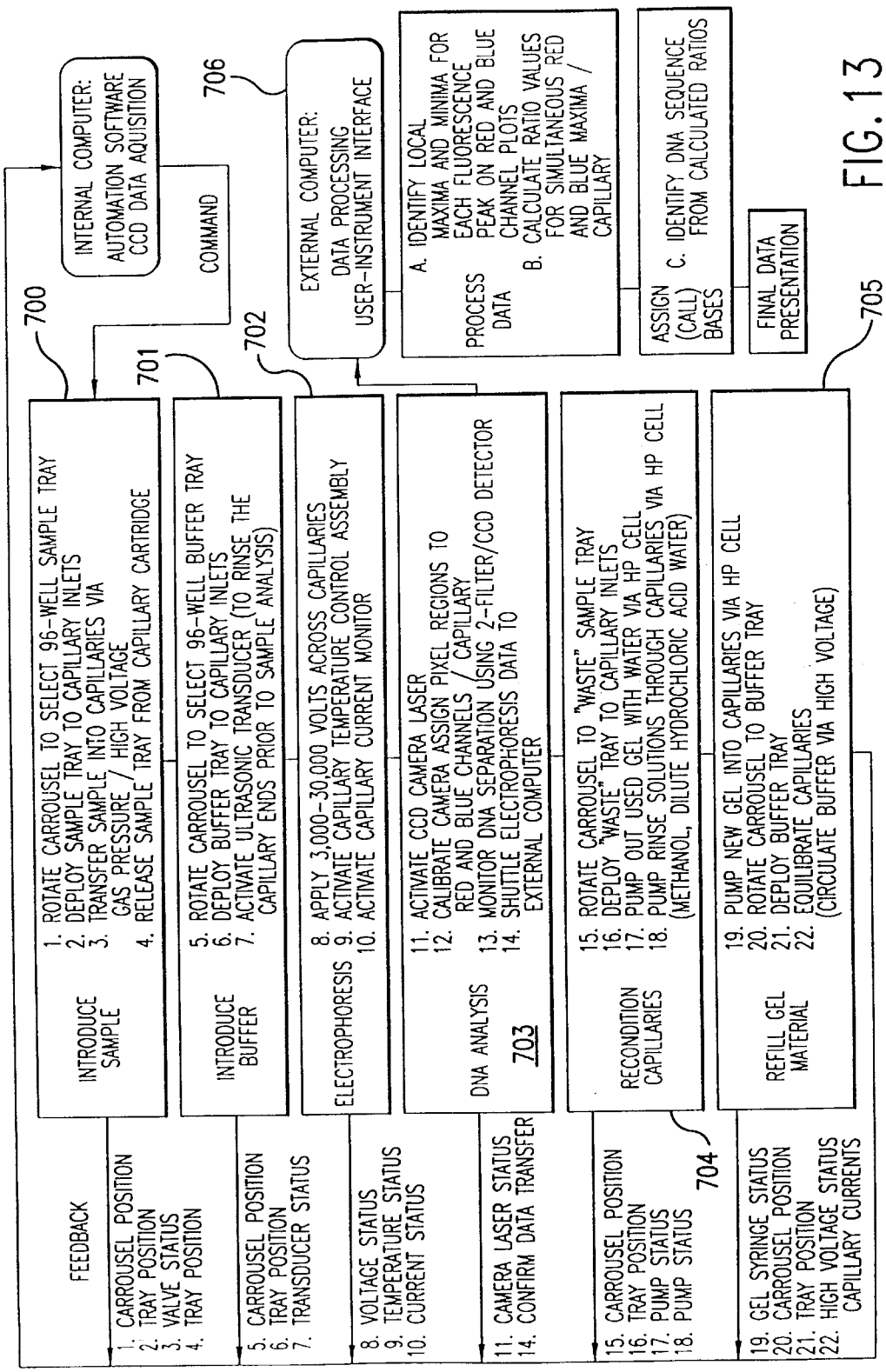
FIG. 13 shows a flowchart illustrating the operation of the present invention.

FIG. 13 explains the operation of the stacked, dual carrousel arrangement which was illustrated in FIG. 11, FIG. 12A and FIG. 12B. After the solvent/gel delivery module 800 fills the capillary array 454 with gel in step 705 as subsequently discussed in detail in FIGS. 14A–C, the controller 404 causes the motor 608 and rotor 604 to rotate the lower carrousel 602 to position the cut-out 620 under the needle array 603 in step 700.1 to prevent the vertical movement of any trays 216, 224 on the lower carrousel 602 in subsequent step 700.2. The controller 404 also commands the motor 608 and rotor 604 to rotate the upper carrousel 601 to position a sample tray 214 under the needle array 603 in step 700.1.

In step 700.2, the controller 404 causes the motor 605 to deploy the sample tray 214 of the upper carrousel 601 to the needle array 603 along the common axis. In step 700.3, the controller 404 increases the gas pressure in the high pressure region 422 or applies a voltage to transfer the sample from the sample tray 214 to the capillary array 454. In step 700.4, the controller 404 causes the motor 605 to move the sample tray 214 away from the needle array 603 along the common axis.

As shown in FIG. 13, the stacked, dual carrousel arrangement sends feedback to the controller 404 which the controller 404 will process to ensure that it issues commands at the proper time. For example, the encoder 612 which is operatively engaged to the rotor 604 sends feedback indicative of the carrousel 601, 602 position 1 to the controller 404. The controller 404 will not issue the command to motor 605 to move the sample tray 214 to the capillary inlets 603 in step 700.2 until the carrousel position feedback 1 indicates that the sample tray 214 on the upper carrousel 601 is beneath the needle array 603.

Similarly, the current meter of the motor 605 sends feedback indicative of the vertical position of the sample tray 2 to the controller 404. The controller 404 will not issue the command to transfer the sample into the capillary array 454 in step 700.3 until the tray position feedback 2 indicates that the sample tray 214 is deployed at the needle array 603.

A pressure transducer of the high pressure region 422 sends the pressure value in the region (valve status 3) to the controller 404. The controller 404 will not issue the command to cause the motor 605 to move the sample tray 214 away from the capillary inlets 603 in step 700.4 until the valve status feedback 3 indicates that the valve of the high pressure region 422 is in the proper position. Finally, the controller 404 will not issue the command to introduce buffer into the capillary array 454 in step 701 until the tray position feedback 2 as determined by the current meter of the motor 605 indicates that the sample tray 214 has been returned to the upper carrousel 601.

Following the completion of step 700 as indicated by the tray position feedback 2, the sequencer module 600 introduces the buffer into the capillary array 454 in step 701. In step 701.5, the controller 404 causes the motor 608 and rotor 604 to rotate the upper carrousel 602 to position its cut-out 620 under the needle array 603. In step 701.5, the controller 404 also causes the motor 608 and rotor 604 to rotate the lower carrousel 602 to position a buffer tray 216 under the needle array 603.

In step 701.6, the controller 404 causes the motor 605 to move the buffer tray 216 from the lower carrousel 602 through the cut-out 620 of the upper carrousel 601 to the needle array 603. In step 701.7, the controller 404 activates an ultrasonic transducer to rinse the capillary inlets 603.

During step 701, the stacked, dual carrousel arrangement sends feedback to the controller 404 which the controller 404 will process to ensure that it issues commands at the proper time. The encoder 612 sends feedback indicative of the lower carrousel 602 position 5 and upper carrousel 601 position 5 to the controller 404. The controller 404 will not issue the command to cause the motor 605 to move the buffer tray 216 to the capillary inlets 603 in step 701.6 until the carrousel position feedback 5 indicates that the cut-out 620 of the upper carrousel 601 and the buffer tray 216 on the lower carrousel 601 are positioned beneath the needle array 603.

Similarly, the current meter of the motor 605 sends feedback indicative of the vertical position of the buffer tray 6 to the controller 404. The controller 404 will not issue the command to activate the ultrasonic transducer in step 701.7 until the tray position feedback 6 indicates that the buffer tray 216 is deployed at the needle array 603. Finally, the ultrasonic transducer sends feedback indicative of its status to the controller 404. The controller 404 will not initiate electrophoresis in step 702 until the transducer status 7 indicates that the capillary inlets 603 have been rinsed.

The stacked, dual carrousel arrangement also performs tasks in step 704 which recondition the capillary array 454 as further explained below in the description of the solvent/gel delivery module of FIG. 14A–C. In step 704.15, the controller 404 causes the motor 608 and rotor 604 to rotate the upper carrousel 602 to position its cut-out 620 under the needle array 603. The controller 404 also causes the motor 608 and rotor 604 to rotate the lower carrousel 604 to position a waste tray 224 under the needle array 603 in step 704.15. In step 704.16, the controller 404 causes the motor 605 to deploy the waste tray 224 from the lower carrousel 602 through the cut-out 620 of the upper carrousel 601 to the needle array 603.

In the preferred embodiment, the controller 404 manages electrophoresis and DNA analysis by issuing commands to the components of the electrophoresis apparatus as described in the discussion of the stacked, dual carrousel arrangement above. Accordingly, the controller 404 manages the tasks enumerated in the left column of FIG. 13. The data processing computer 406 is devoted to processing the data obtained from executing DNA analysis (Step 703) since DNA data processing is typically computationally intensive. Accordingly, the data processing computer 406 performs the tasks enumerated in the right column of FIG. 13. The controller 404 and data processing computer 406 are connected to a local area network and communicate via a data processing user-instrument interface 706.

Figure 14A:
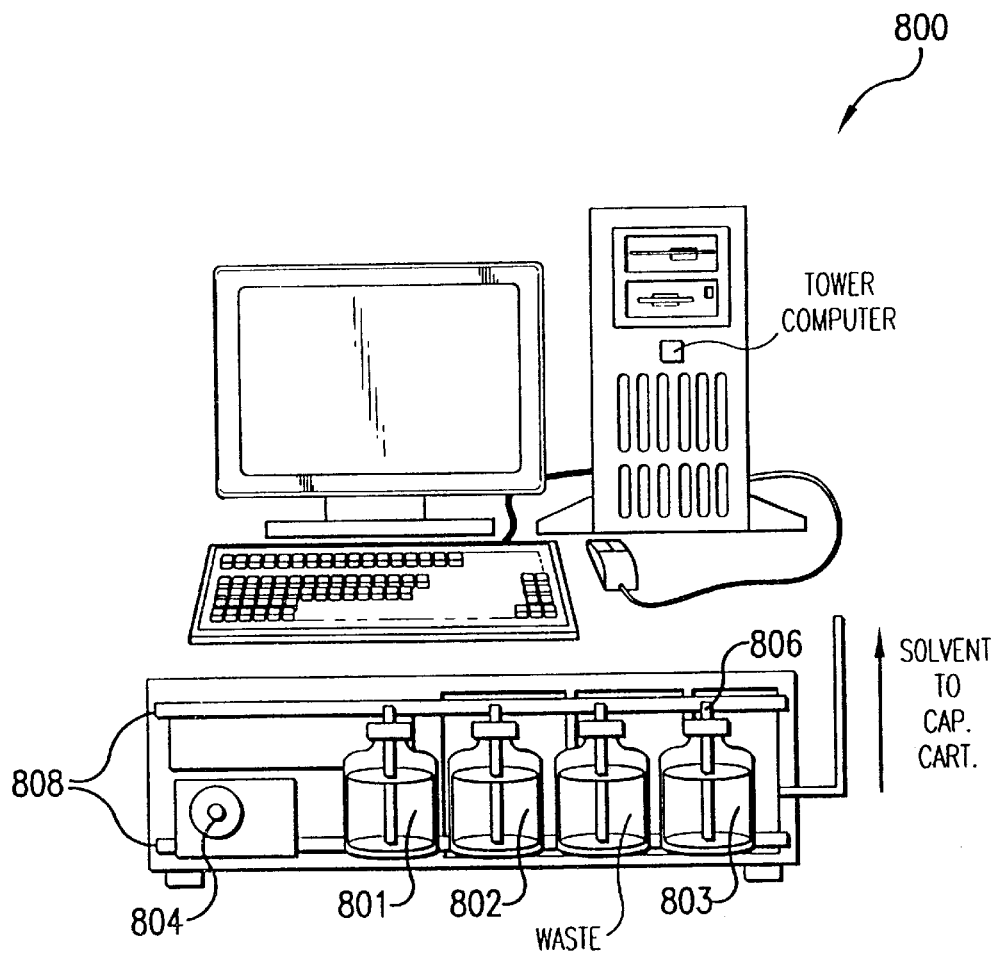
FIGS. 14A–C show a front, side and back view of the solvent/gel delivery module within the system.
Figure 14B:
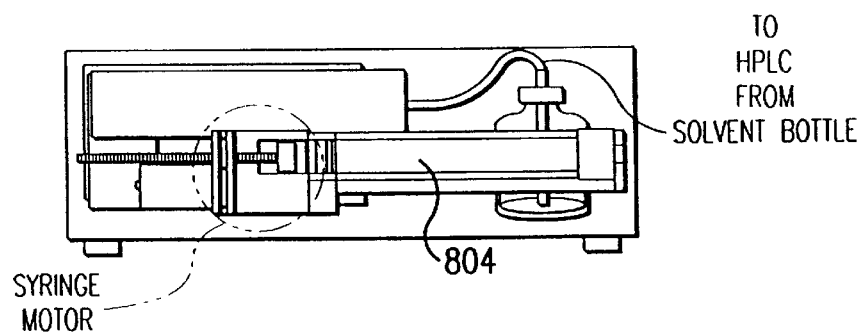
Figure 14C:
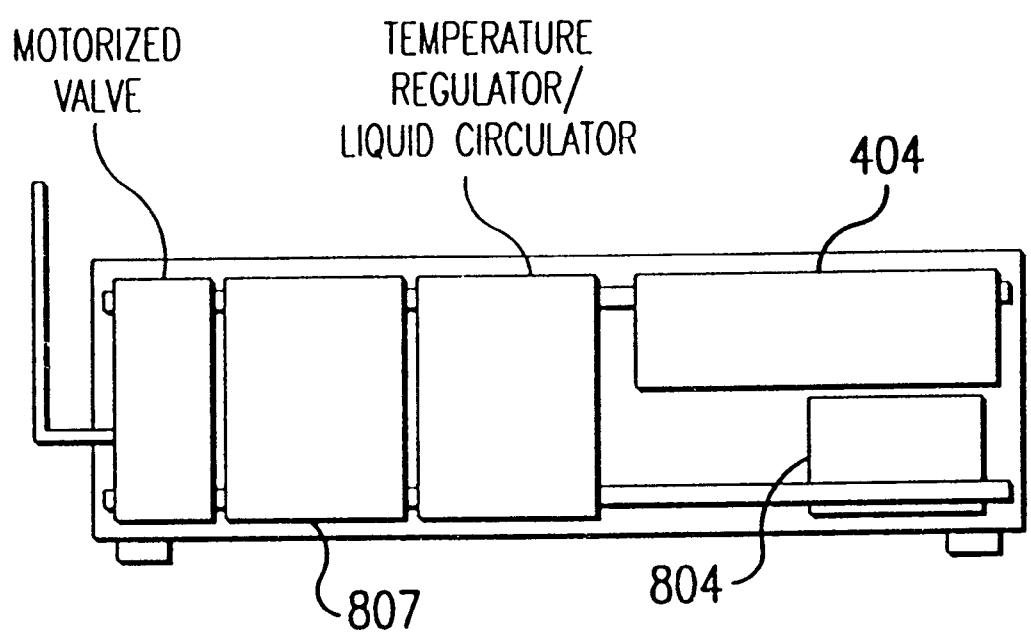

FIGS. 14A–C illustrate the solvent/gel delivery module 800 which is used after DNA analysis to recondition the capillary array 454 and to refill the capillary array 454 with gel. FIGS. 14A, 14B and 14C show a front view, a side view and a back view respectively of the solvent/gel delivery module 800. During DNA analysis, the sample travels from the capillary inlets 603 in FIG. 11 through the capillary array 454 from right to left.

During capillary reconditioning, the solvent travels from the solvent containers 801–803 shown in FIG. 14A, through the solvent/gel input port 606 shown in FIG. 11 and through the capillary array 454 of the sequencer module 600 of FIG. 11 from left to right. Similarly, during refill of the capillary array 454 with gel, the gel travels from the gel syringe 804 shown in FIG. 14B, through the solvent/gel input port 606 shown in FIG. 11 and through the capillary array 454 of the sequencer module 600 of FIG. 11 from left to right.

The solvent containers 801, 802, 803 hold methanol, water and soap respectively. A feeder tube 806 in each solvent container 801–803 carries solvent toward a HPLC pump and wash solvent system 807. As in the previously described embodiments, the wash solvent system 807 includes a high pressure cell (HP cell) to create increased pressures for faster reconditioning of the capillary array 454.

Support rails 808 provide the structure necessary to hold the components of the solvent/gel delivery module 800 including the solvent containers 801–803, the gel syringe 804, the HPLC pump and wash solvent system 807 and the controller 404. The controller 404 causes the other components of the solvent/gel delivery module 800 to recondition the capillary array 454 and to refill the capillary array 454 with gel material.

Figure 15A:
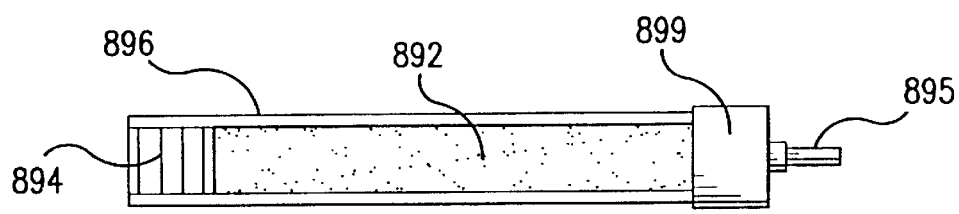
FIG. 15A–C shows a detailed view of a gel syringe contained the gel delivery module.
Figure 15B:
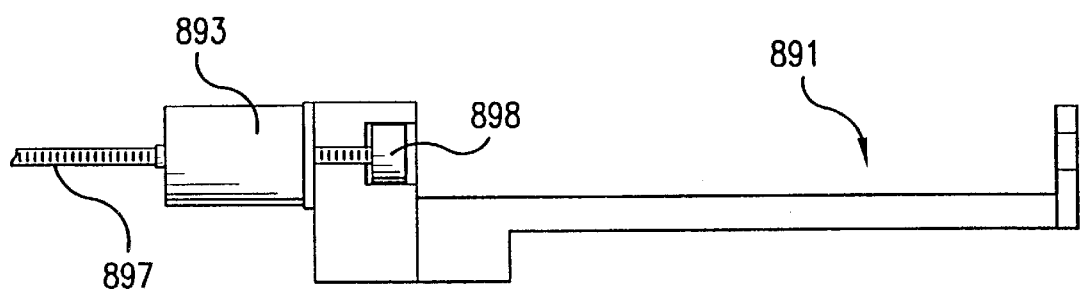
Figure 15C:
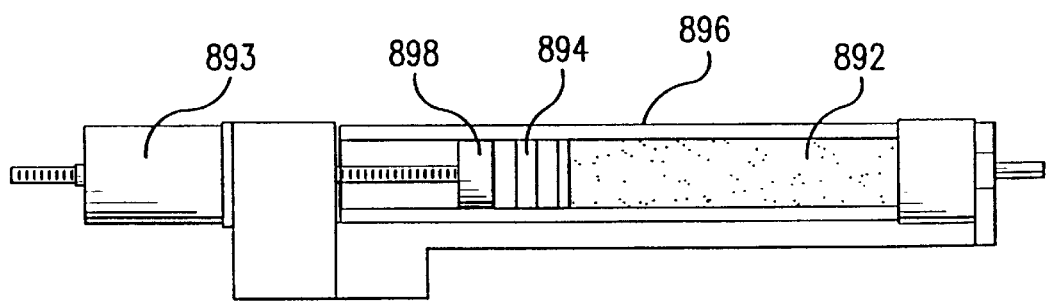

FIGS. 15A–C illustrates the gel syringe 804 of FIG. 14B in more detail. In contrast to the solvent in the solvent containers 801–803, the gel is too viscous to be delivered by a pump. Accordingly, the electrophoresis apparatus uses a gel syringe 804 for gel delivery. The gel syringe 804 contains a gel tube carriage 891 which holds a gel cartridge containing gel material 892. Since the gel cartridge is disposable, it can be removed from the gel tube carriage 891 after refill of the capillary array 454 with gel material and replaced with a new gel cartridge for use in a subsequent execution of electrophoresis and DNA analysis.

A stepper motor linear actuator 893 has a movable actuator shaft 897 provided with a pushing member 898. The pushing member 898 abuts a surface on a teflon plunger 894 located at one end of the gel syringe 804, causing the gel material to flow through a syringe cap 899 and a high pressure fitting 895 at the other end of the gel syringe 804. The controller 404 shown in FIG. 14C selectively activates the stepper motor linear actuator 893 to control gel delivery. A cylindrical tube 896 forms the outer structure of the gel syringe 804. O-rings prevent the gel material 892 from leaking around the teflon plunger 894 as it moves toward the high pressure fitting 895.

In the preferred embodiment, the stepper motor linear actuator, available from A.M.S.I Corporation in Smithtown, N.Y. can exert 140 lbs of linear force and displaces 10 ml of gel in 6,000 pulses. The cylindrical tube 896 is composed of standard acrylic material and the syringe cap 899 is composed of stainless steel. The high pressure fitting 895 is available from Swagelock.

Figure 16:
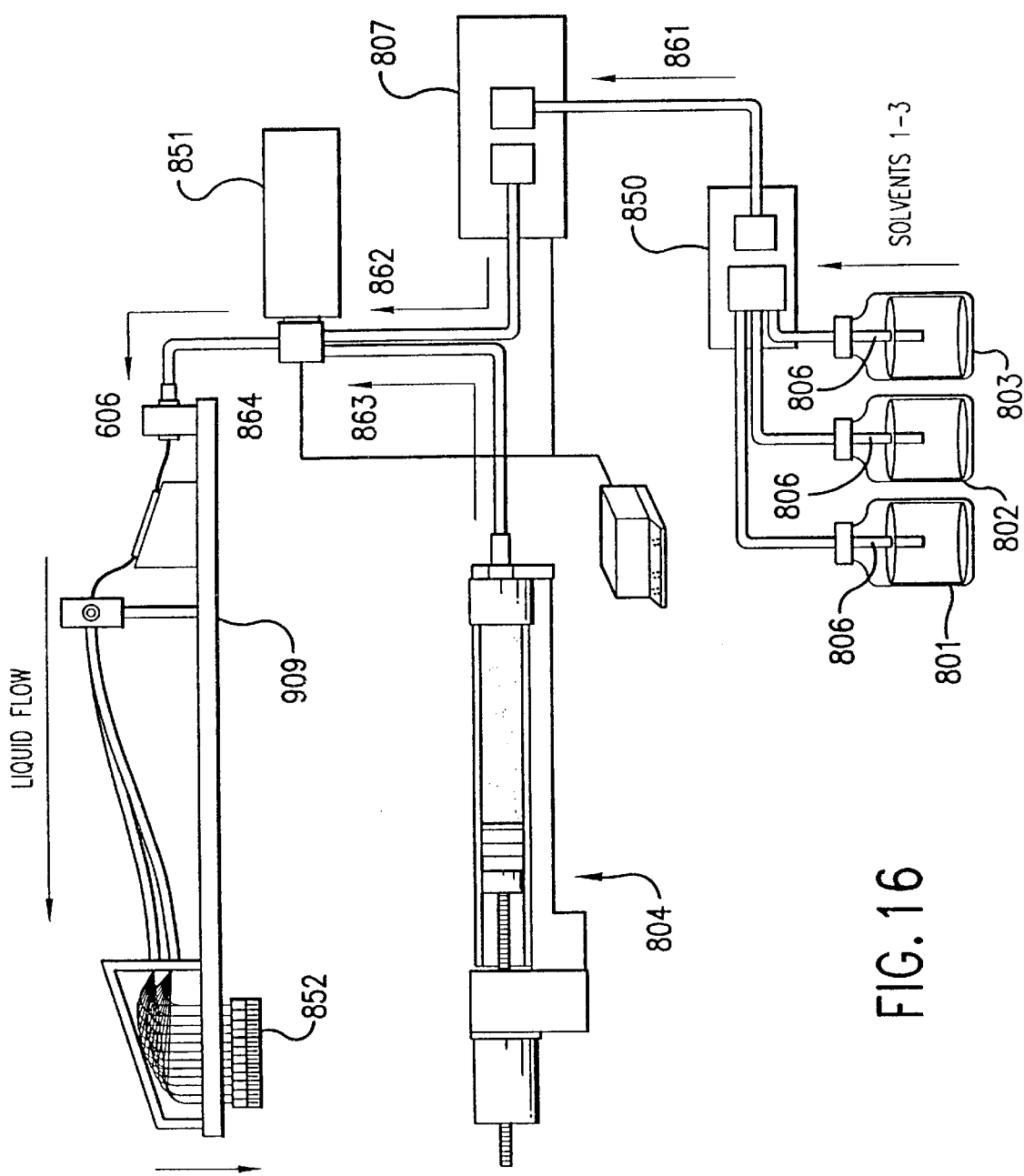
FIG. 16 shows the flow of gel and solvent through the solvent/gel delivery module to the sequencer module.

FIG. 16 illustrates the integration of the gel syringe 804 and the HPLC wash solvent system 807 into the solvent/gel delivery module 800. A solvent manifold 850 connects three inlets from the feeder tubes 806 of the solvent containers 801–803 to an outlet. Feeder tubes 806 from the solvent containers 801–803 are connected to the inlets of the solvent manifold 850 by tubing 860. The controller 404 pictured in FIG. 14C controls the solvent manifold 850 to select solvent from one of the three solvent containers 801–803. The inlet of the HPLC pump 807 is connected to the outlet of the solvent manifold 850 by tubing 861 and the outlet of the HPLC pump 807 is connected to an inlet of a valve manifold 851 by tubing 862.

The valve manifold 851 connects two inlets and an outlet. One inlet of the valve manifold 851 is connected to the gel syringe 804 by tubing 863 and the other inlet of the valve manifold 851 is connected to the outlet of the HPLC pump 807. The outlet of the valve manifold 851 is connected to the solvent/gel input port 606 by tubing 864. The controller 404 pictured in FIG. 14C causes the valve manifold 851 to select either the inlet connected to the gel syringe 804 or the inlet connected to the HPLC pump 807.

In the preferred embodiment, the tubing 860 connecting the feeder tubes 806 of the solvent containers 801–803 to the inlets of the solvent manifold 850 is standard teflon tubing with a diameter of 1/8 inches. The tubing 861 connecting the outlet of the solvent manifold 850 to the inlet of the HPLC pump 807 is peek tubing with a diameter of 1/16 inches. The tubing 861 connecting the outlet of the solvent manifold 850 to the inlet of the HPLC pump 807, the tubing 862 connecting the outlet of the HPLC pump 807 to an inlet of the valve manifold 851, the tubing 863 connecting the gel syringe 804 to an inlet of the valve manifold 851 and the tubing 864 connecting the outlet of the valve manifold 851 to the solvent/gel input port are peek tubing with a diameter of 1/16 inches.

In the preferred embodiment, the HPLC pump 807, available from Alltech Corporation (Model Number 301300), has a nonmetal pump head. The valve manifold 851 is a nonmetal valve, available from Alltech Corporation (Model Number 97500).

FIG. 13 explains the operation of the solvent/gel delivery module 800 which was illustrated in FIG. 14A and FIG. 16. Following DNA analysis in step 703, the proper rotational positioning of the carrousels 601, 602 in step 704.15 and the proper deployment of the waste tray in step 704.16, the controller 404 causes the solvent/gel delivery module 800 to pump out the used gel from the capillary array 454 via the HP cell in step 704.17.

To pump out the used gel, the controller 404 causes the solvent manifold 850 to select the inlet from the water container 802 and causes the valve manifold 851 to select the inlet from the HPLC pump 807 as shown in FIG. 16. The HPLC pump 807 pumps water from the solvent manifold 850 through the valve manifold 851 to the HP cell to create increased pressures for faster reconditioning of the capillary array 454 as previously described. The waste tray 852 which was properly deployed in step 704.16 collects the used gel from the capillary array 454.

After the gel has been removed from the capillary array 454, the controller 404 causes the solvent/gel delivery module 800 to pump rinse solutions through the capillary array 454 via the HP cell in step 704.18. To perform this rinsing, the controller 404 causes the solvent manifold 850 to select the inlet from the methanol container 801 and causes the valve manifold 851 to select the inlet from the HPLC pump 807 as shown in FIG. 16. The HPLC pump 807 pumps methanol from the solvent manifold 850 through the valve manifold 851 to the HP cell to create increased pressures for faster rinsing of the capillary array 454 as previously described. The waste tray 852 which was properly deployed in step 704.16 collects the used solvent from the capillary array 454.

After rinsing the capillary array 454 with methanol, the controller 404 causes the solvent/gel delivery module 800 to perform rinsing of the capillary array 454 with soap from container 803. To perform this rinsing, the controller 404 causes the solvent manifold 850 to select the inlet from the soap container 803 and causes the valve manifold 851 to select the inlet from the HPLC pump 807 as shown in FIG. 16. The HPLC pump 807 pumps soap from the solvent manifold 850 through the valve manifold 851 to the HP cell to create increased pressures for faster rinsing of the capillary array 454 as previously described. The waste tray 852 which was properly deployed in step 704.16 collects the used solvent from the capillary array 454. Further, the controller 404 causes the solvent/gel delivery module to repeat the reconditioning process with the solvents from the three solvent containers 801–803 until the capillary array 454 is clean.

As shown in FIG. 13, the solvent/gel delivery module sends feedback to the controller 404 which the controller 404 will process to ensure that it issues commands at the proper time. For example, the controller 404 will not cause the gel/solvent delivery module 800 to pump rinse solutions through the capillary array 454 until the HP pump status feedback 17 indicates that the gel has been pumped from the capillary array 454. Similarly, the controller 404 will not issue the command to refill the capillary array with gel material in step 705 until the HP pump status feedback 18 indicates that the capillary array 454 has been rinsed with methanol and soap.

In the preferred embodiment, the controller 404 will determine the HP pump status feedback 17. The controller 404 determines the HP pump status feedback 17 by computing the volume of solution which has passed through the capillary array 454 from the flow rate of the HP pump specified by the manufacturer and the amount of time which has elapsed since the pump was activated.

Following the reconditioning of the capillaries in step 704, the controller 404 causes the solvent/gel delivery module 800 to refill the capillary array 454 with new gel via the HP cell in step 705.19. To refill the capillary array 454 with new gel, the controller 404 causes the valve manifold 851 to select the inlet from the gel syringe 804 as shown in FIG. 16. The gel syringe 804 delivers gel through the valve manifold 851 to the HP cell to create increased pressures for faster refilling of the capillary array 454 as previously described. The waste tray 852 which was properly deployed in step 704.16 collects any solvent or gel which leaves the capillary array 454 during step 705.19.

After filling the HP cell and capillary array 454 with gel in step 704.18, the process can continue in one of two ways. In one embodiment, the gel in the HP cell can be used as the buffer in the subsequent electrophoresis of step 702. In this embodiment, the process continues with step 705.20. In an alternate embodiment, the controller 404 causes the solvent/gel delivery module to pump the gel from the HP cell and to fill it with buffer using a process similar to step 704 before proceeding to step 705.20.

The dual, stacked carrousel participates in the remaining tasks of step 705. In step 705.20, the controller 404 causes the rotor 604 to rotate the upper carrousel 602 to position its cut-out 620 under the needle array 603. The controller 404 also causes the rotor 604 to rotate the lower carrousel 604 to position a buffer tray 216 under the needle array 603 in step 705.20. In step 705.21, the controller 404 causes the motor 605 to deploy the buffer tray 216 from the lower carrousel 602 through the large opening of the upper carrousel 601 to the needle array 603.

Step 705 concludes with a step to equilibrate the capillary array 454 and to circulate buffer through the capillary array 454 (Step 705.22). Differences in drag through the capillary array 454 will cause air bubbles and pressure differences to develop within the gel in the capillary array 454 during gel delivery in step 705.19. Step 705.22 removes the pressure differences and air bubbles with a procedure to equilibrate the capillary array 454 and circulate buffer through the capillary array 454. This procedure is similar to the electrophoresis executed in step 702 except DNA is absent from the capillary array 454 during step 795.22 while DNA is obviously present during electrophoresis of step 702. Specifically, a voltage is applied across the capillary array 454 to induce relaxation of the gel and movement of the buffer through the capillary array 454. After circulating the buffer in the capillary array 454 in step 705.22, the process repeats for the next DNA analysis beginning with sample introduction in step 700.

As shown in FIG. 13, the solvent/gel delivery module continues to send feedback to the controller 404 in step 705 as it did in step 704. The controller 404 will process the feedback to ensure that it issues commands at the proper time. For example, the controller 404 will not execute any commands beyond step 705.19 until the gel syringe feedback 19 indicates that the capillary array 454 has been filled with new gel. Similarly, the controller 404 will not issue the command to rotate the upper carrousel 601 and lower carrousel 602 in step 705.20 until the HP pump status feedback 19 indicates that the gel has been pumped into the capillary array 454.

In the preferred embodiment, the controller 404 will determine the gel syringe feedback 19. The controller 404 determines the gel syringe feedback 19 by computing the volume of solution which has passed through the capillary array 454 from the displacement rate of the gel syringe and the amount of time which has elapsed since the gel syringe was activated.

Similarly, the encoder which is operatively engaged to the rotor 604 sends feedback indicative of the position of the carrousels 20 to the controller 404 in step 705. The controller 404 will not issue the command to deploy the buffer tray 216 in step 705.21 until the carrousel position feedback indicates that the large opening of the upper carrousel 601 and the buffer tray 216 on the lower carrousel 601 are positioned beneath the needle array 603.

The current meter of the vertical motor drive 605 also sends feedback indicative of the vertical position of the buffer tray 6 to the controller 404. The controller 404 will not issue the command to circulate the buffer in the capillary array 454 in step 705.22 until the tray position feedback 21 indicates that the buffer tray 216 is deployed at the needle array 603. Finally, the controller 404 receives feedback on the high voltage status of the capillary currents 22. The controller 404 will not proceed to step 700 to introduce the next DNA sample until the high voltage status 22 indicates that the buffer has been circulated through the capillary array 454.

Figure 17:
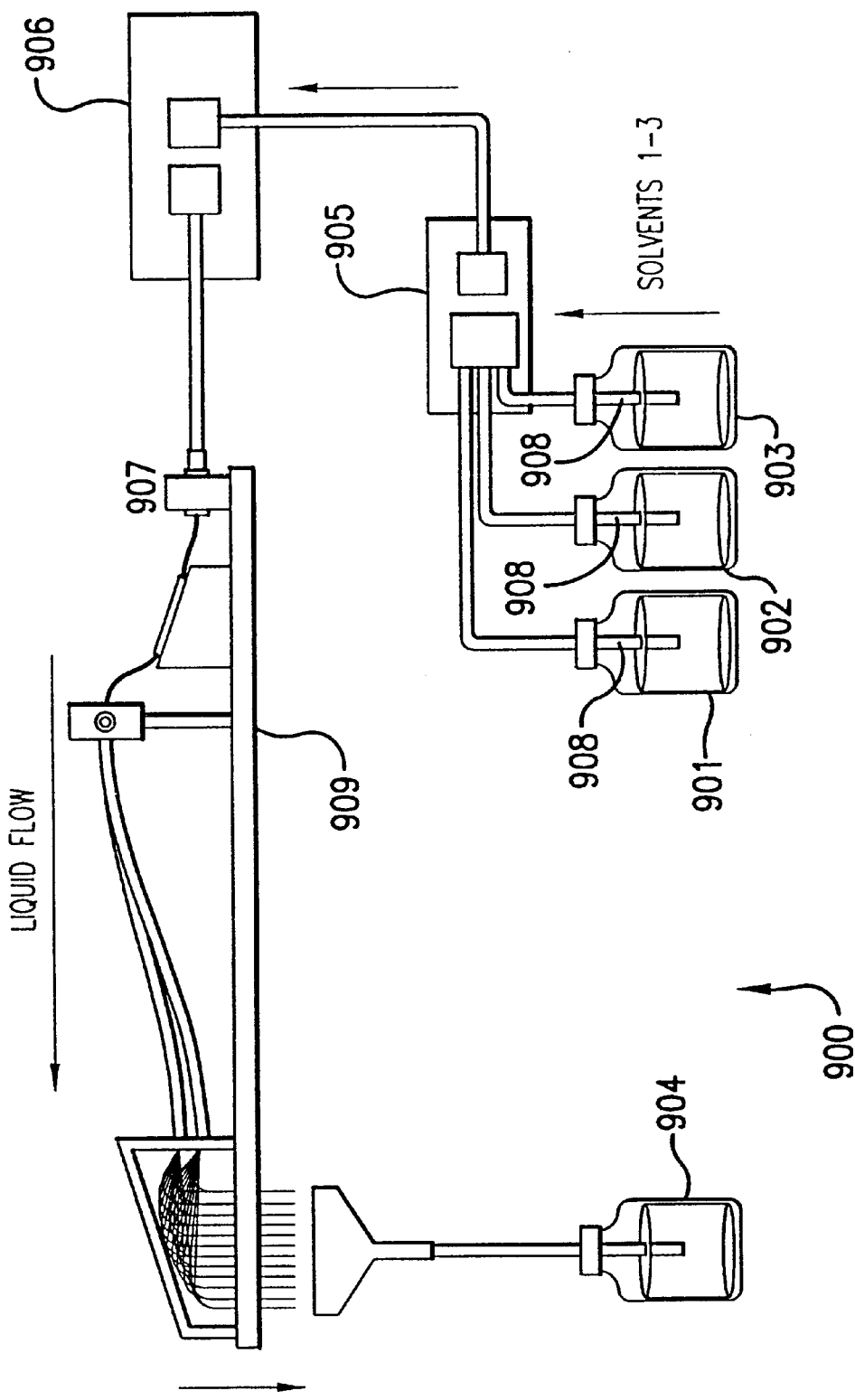
FIG. 17 shows the off-line capillary reconditioner.

FIG. 17 illustrates an off-line capillary reconditioner 900 which is used periodically to thoroughly clean a capillary cartridge 909. To thoroughly clean the capillary cartridge 909, the operator removes it from the automatic electrophoresis system and installs it in the off-line capillary reconditioner 900. Accordingly, the operator can install another clean capillary cartridge 909 in the automatic electrophoresis system and execute DNA analysis with that capillary cartridge while the off-line capillary reconditioner 900 is thoroughly cleaning the previously used capillary cartridge 909. Since a through cleaning typically takes twenty to thirty minutes, the off-line capillary reconditioner improves the throughput of the automatic electrophoresis system as the system does not have to wait for a thorough cleaning of the capillary cartridge 909 between consecutive executions of DNA analysis.

The off-line capillary reconditioner 900 is a low-cost streamlined version of the solvent/gel delivery module 600 previously explained in FIG. 11 as it does not contain all of the items included in the solvent/gel delivery module 600.

For example, the off-line capillary reconditioner 900 does not have a camera, a laser, or a gel syringe. The off-line capillary reconditioner 900 does not include a gel syringe for gel delivery because undesirable hardening of the gel could occur at the ends of the capillary array 454 during movement of the capillary cartridge from the off-line capillary reconditioner 900 to the automatic electrophoresis system if the gel were delivered off-line prior to movement of the capillary cartridge. The streamlined nature of the off-line capillary reconditioner 900 gives it the advantage of increasing the throughput of the system with a low cost.

The solvent containers 901, 902, 903 hold methanol, water and soap respectively. A feeder tube 908 in each solvent container 901–903 carries solvent toward a solvent manifold 905. The solvent manifold 905 connects three inlets to one outlet. The three inlets of the solvent manifold are connected to the feeder tubes 906 of the solvent containers 901–903 to establish a one to one correspondence between the set of inlets and the set of feeder tubes 906.

A HPLC pump 906 has one inlet, which is connected to the outlet of the solvent manifold, and one outlet, which is connected to the solvent input port 907 at one end of the capillary cartridge 909. The off-line capillary reconditioner 900, like the solvent/gel delivery module 600 described in FIG. 14A, also has a HP cell to create increased pressures for faster reconditioning of the capillary cartridge 909. A controller manages the operation of the solvent manifold 905 and HPLC pump 906. A waste container 904 collects waste during capillary reconditioning at the other end of the capillary cartridge 909.

In the preferred embodiment, the controller is a simple, low-cost digital signal processing system which receives status feedback and issues commands to the HPLC pump 906 and the solvent manifold 905 in a predetermined order as explained below. Alternatively, a general purpose computer like a personal computer could be used to execute a simple control program to manage the off-line capillary reconditioner.

After the operator installs the capillary cartridge 909 in the off-line capillary reconditioner 900, the internal controller causes the solvent manifold to select the inlet from the water container 901 and activates the HPLC pump 906. The HPLC pump 807 pumps water from the solvent manifold 850 to the HP cell to create increased pressures for faster reconditioning of the capillary cartridge 909 as previously described. The waste container 904 which was properly deployed previously collects the used gel from the capillary cartridge 909.

After the gel has been removed from the capillary cartridge 909, the off-line capillary reconditioner 900 rinses the capillary cartridge 909 via the HP cell with methanol. First, the controller causes the solvent manifold 905 to select the inlet from the methanol container 902. The HPLC pump 906 pumps methanol from the solvent manifold 905 to the HP cell to create increased pressures for faster rinsing of the capillary cartridge 909. The waste container 904 which was properly deployed previously collects the used solvent from the capillary cartridge 909.

Next, the off-line capillary reconditioner 900 rinses the capillary cartridge 909 via the HP cell with soap from container 903. First, the controller causes the solvent manifold 905 to select the inlet from the soap container 903. The HPLC pump 906 pumps the soap from the solvent manifold 905 to the HP cell to create increased pressures for faster rinsing of the capillary cartridge 909. The waste container 904 which was properly deployed previously collects the used solvent from the capillary cartridge 909. Further, the controller 404 causes the off-line capillary reconditioner 900 to repeat the reconditioning process with the solvents from the three solvent containers 801–803 until the capillary array 454 is clean.

Figure 18:
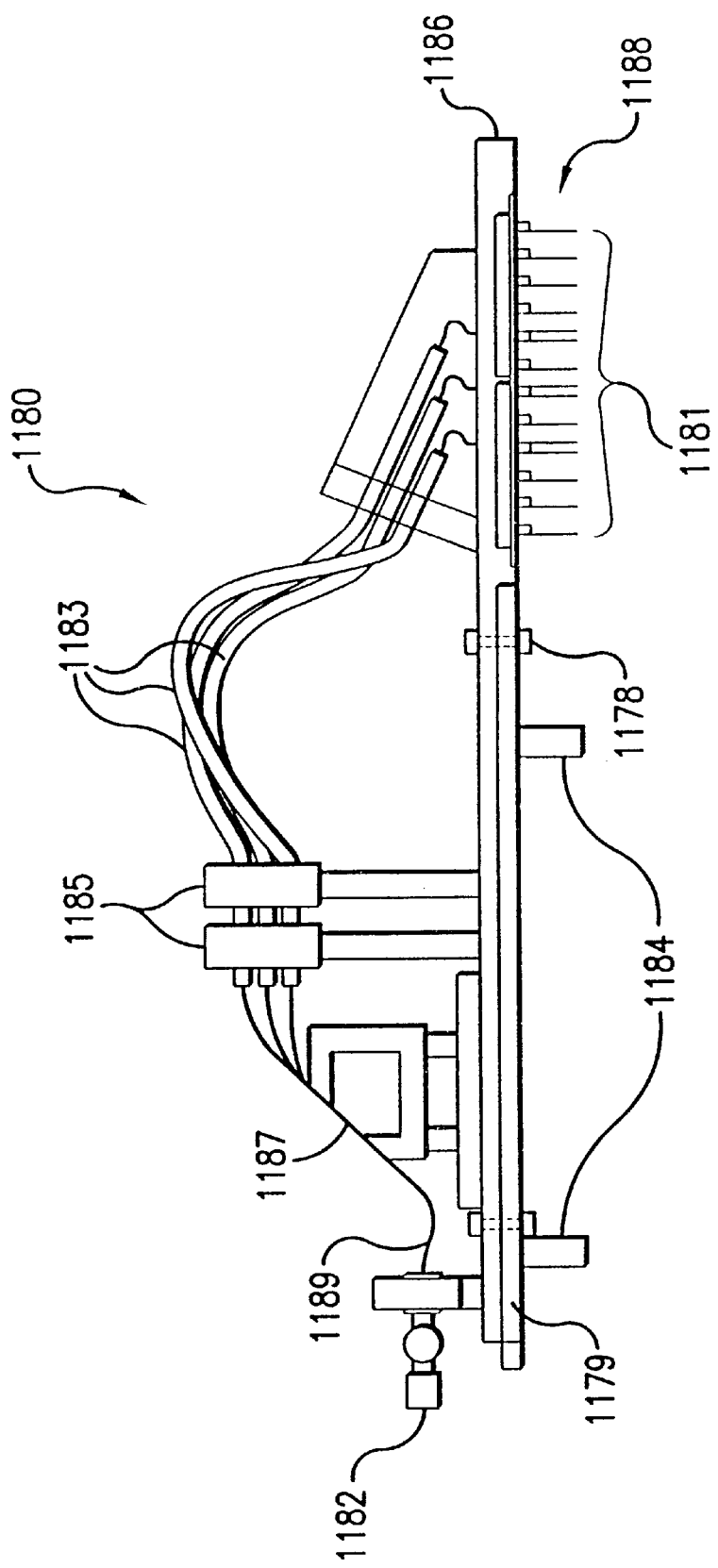
FIG. 18 is a side view of capillary cartridge of the present invention.

FIG. 18 illustrates another preferred embodiment of the capillary cartridge 1180. In this embodiment, the capillary tubes run from their first ends 1188 disposed in an electrode/capillary array 1181. The capillary tubes, then, run inside multilumen tubing 1183. The multilumen tubing is taught in detail in U.S. patent application Ser. No. 08/866,308, which is incorporated by reference herein. The multilumen tubing 1183 is held firmly in place by tubing holders 1185. The capillary tubes, without the protection the multilumen tubing, pass through an optical detection region 1187. Beyond the optical detection region 1187, the capillary tubes have a common termination and are bundled together and cemented into a high pressure T-shaped fitting 1182 made from electrically conductive material, which, during electrophoresis, is connected to electrical ground.

The tubing holders 1185 and the T-fitting 1182 are fixed to a cartridge base 1186. The cartridge base 1186 is made from polycarbonate plastic for its dielectric characteristic. The base 1186 in turn is removably attached to a shuttle 1179 which includes a set of rail couplings 1184 protruding from its bottom. These rail couplings 1184 are arranged so that they fit on to a railing system (not shown in FIG. 18) of the sequencer module 400 in FIG. 10 or 600 in FIG. 11. The railing system allows the shuttle 1184 to move between an in position and out position. The base 1186 is detached from the shuttle 1179 so that the cartridge 1180 is disposed (or cleaned) and a new (or cleaned) capillary cartridge is attached when the shuttle 1179 is in its out position. The combination of the railing system and the shuttle 1179 allows the newly attached capillary cartridge to be repeatedly located at the same position as that of the disposed capillary cartridge in relation to a camera and a laser (not shown in FIG. 18) when the shuttle 1179 is in its in position.

In a preferred embodiment, the shuttle 1179 extends the length of the base 1186 with an opening to accommodate the electrode/capillary array 1181; the shuttle 1179 is attached to the base 1186 by a plurality of removable fasteners 1178.

Figure 19:
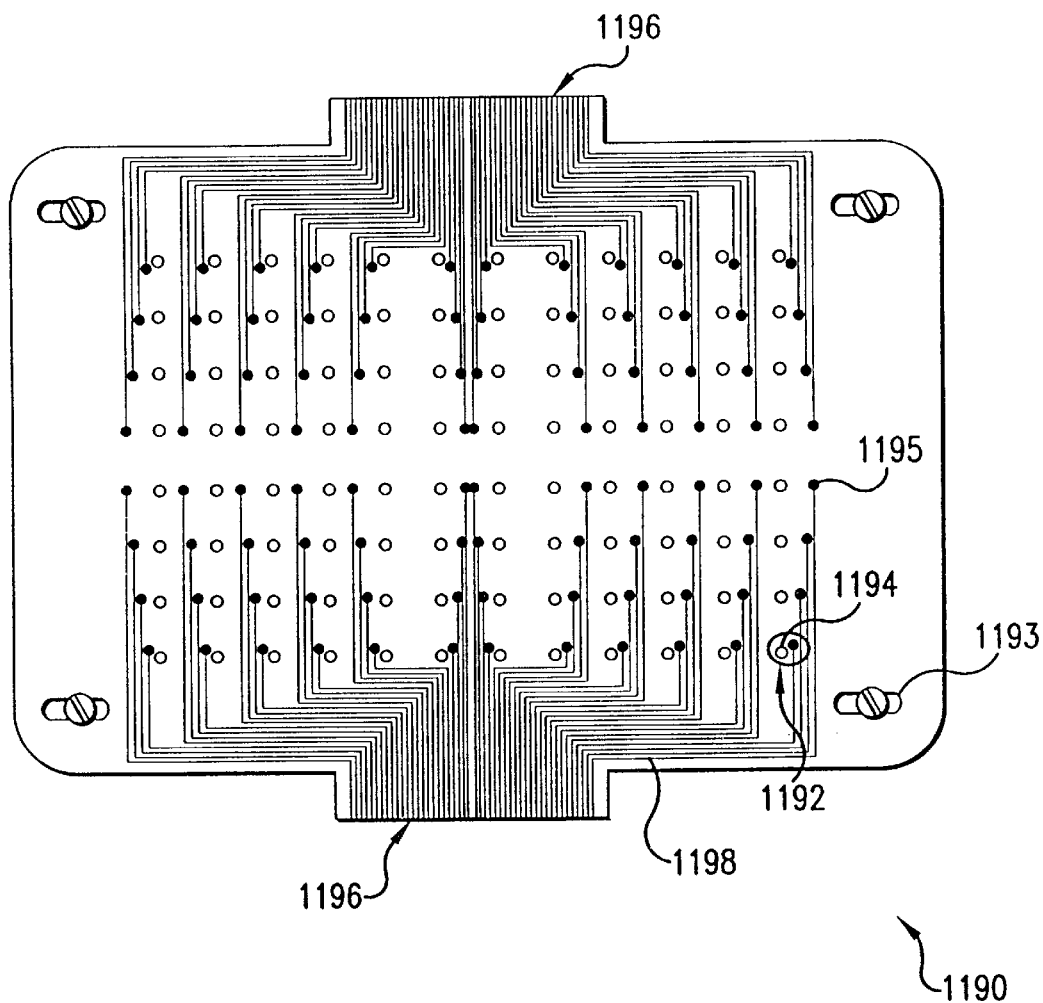
FIG. 19 is a view of a current supply/monitoring board.

The electrode/capillary array 1181 is held in place by a current supply/monitoring board 1190 depicted in FIG. 19. The board 1190 is preferably a printed circuit board for supplying high voltage.

The board 1190 preferably includes a plurality of large holes 1193 so that a set of fasteners can be used to attach the board 1190 to the base 1186. However, any other means, e.g., gluing, can be utilized as well to attach the board 1190 to the base 1186.

The board 1190 also includes a plurality of tube holes 1194 arranged to be co-located with holes in the base 1186 to allow the first ends of the capillary tubes to protrude through the tube holes 1194 when the board 1190 is attached to the base 1186. The plurality of pins 1195, preferably gold plated, are also disposed on the board 1190. At least one pin is placed proximate to each tube hole forming a pin-hole pair 1192. Each pin-hole pair is dipped into one sample well of the sample microtitre tray.

The board 1190 further includes high voltage electrical wire leads 1198. The wire leads 1198 electrically connect each pin 1195 to corresponding connector ends 1196 formed on the periphery of the board 1190. Each connector end 1196 is shaped to receive a high voltage connector which preferably includes about 50 electrical connections. The high voltage connectors then connect the wire leads 1198 to power supply lines from a high voltage power supply, preferably manufactured by Bertan (not shown in FIG. 19). This establishes a closed electrical circuit from the pins 1195 to a second electrode connected to the high pressure T-fitting 1182 when the capillary tubes are filled with gel. The second electrode is preferably connected to the system ground.

In addition, the high voltage connectors are also connected to an electronic current monitor which monitors the electric currents. In the current monitor, the current flowing in each power supply line is preferably monitored in multiple power supply lines at a time and in sequence. This allows the current monitor to make integrated current measurements.

Figure 20:
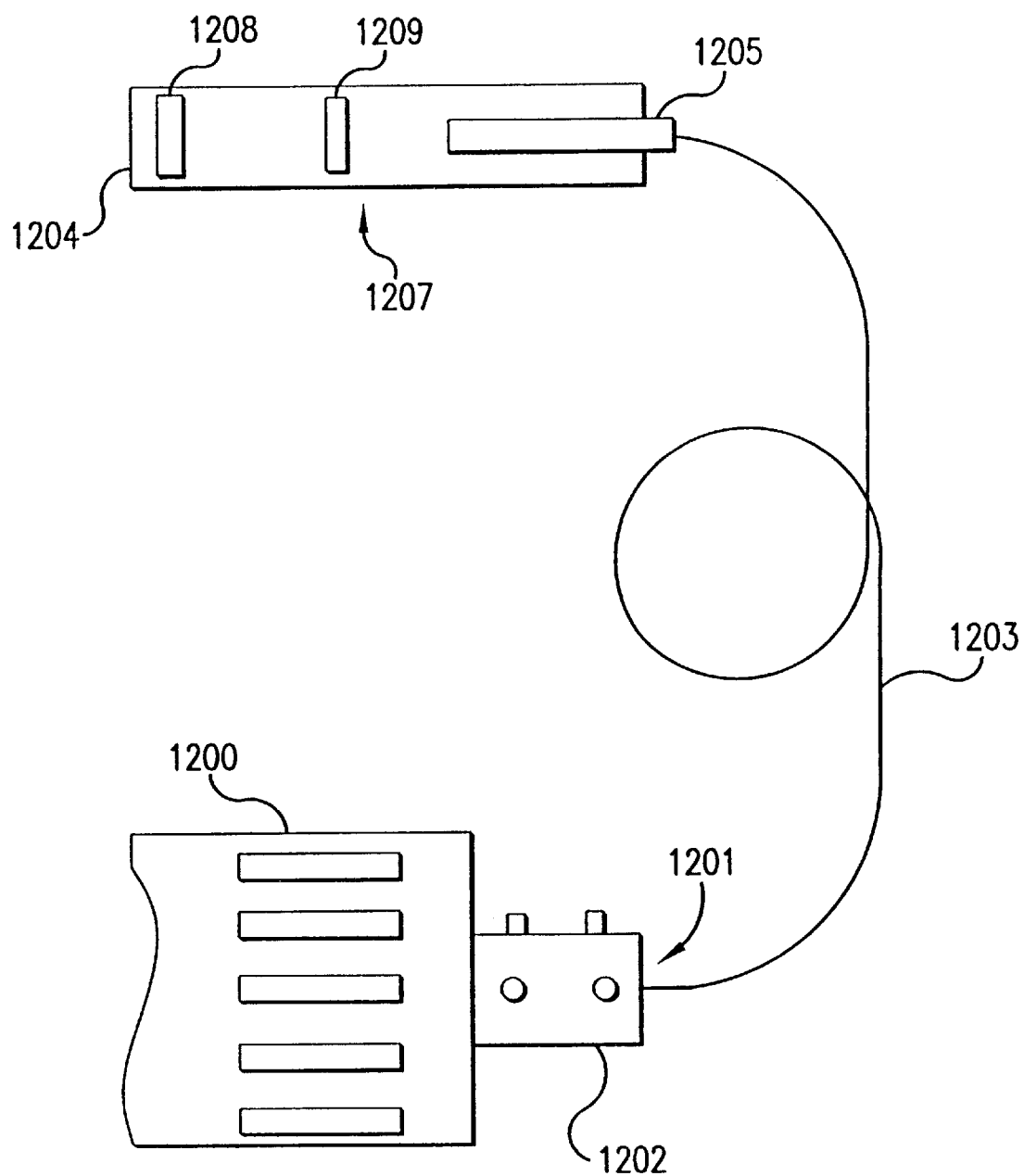
FIG. 20 shows a multi-wavelength beam generator using one laser head.

FIG. 20 illustrates a multi-wavelength beam generator. The beam generator includes a laser head 1200, preferably an argon ion laser capable of producing multi-wavelength laser beams in the wavelengths of 457 nm, 476 nm, 488 nm, 496 nm, 502 nm, 514 nm. The beam generator also includes a laser emitter tube 1207, which is connected to the argon ion laser 1200 by an optical coupling assembly 1202.

The optical coupling assembly 1202 include a fiber coupler 1201, which is connected to the laser head 1200, and an optical fiber cable 1203, which connects the fiber coupler 1201 with the laser emitter tube 1207. The fiber coupler 1201 optically aligns the laser head 1200 with the fiber cable 1203 which is an a chromic optical fiber cable. This optical coupling assembly 1202 permits the laser emitter tube 1207 to be remotely located from the laser head 1200 and still produce laser beams, coherent light, at the laser emitter tube 1207. This also allows the laser head 1200, which generates heat, to be located in a less sensitive area of the sequencer.

The laser emitter tube 1207 includes a one dimensional focuser 1208, preferably a positive cylindrical optical lens with 10 cm focal length, located at an output end 1204 of the laser emitter tube 1207. The laser emitter tube 1207 also includes a fiber emitter tube 1205 receiving the optical fiber cable 1203 and a beam expander 1209, preferably a negative cylindrical optical lens with 1.9 cm focal length, placed between the fiber emitter tube 1205 and the one dimensional focuser 1208. The laser emitter tube 1207 is preferably housed in a 1" dia.×6" long tube.

Figure 22A:
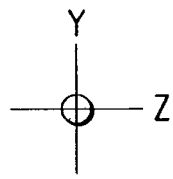
FIG. 22A illustrates a light beam foot print at the output of a laser emitter.
Figure 22B:
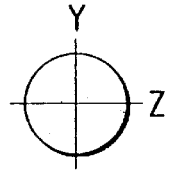
FIG. 22B illustrates a light beam foot print after a beam expander.
Figure 22C:
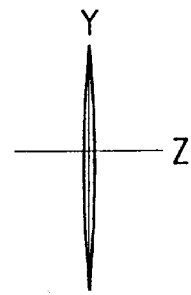
FIG. 22C illustrates a light beam foot print after a one-dimensional focus lens.
Figure 22:
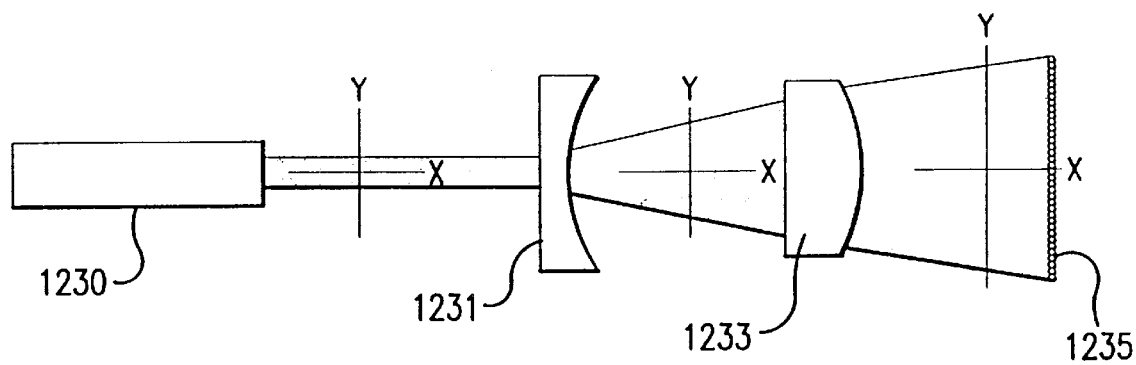
FIG. 22 shows optical processing functions of a laser emitter tube.

FIG. 22 schematically depicts the optical processes performed by the laser emitter tube 1207. The laser light emitted by the fiber emitter tube 1230 is expanded by the beam expander 1231. The laser beam then is focused in only one direction by the one dimensional focuser 1233. The resulting beam is directed toward the capillary array 1235. The resulting laser beam is narrowed in one direction and elongated in the other direction. FIGS. 22A–C illustrates the foot prints of the laser beams at each processing step.

Figure 21:
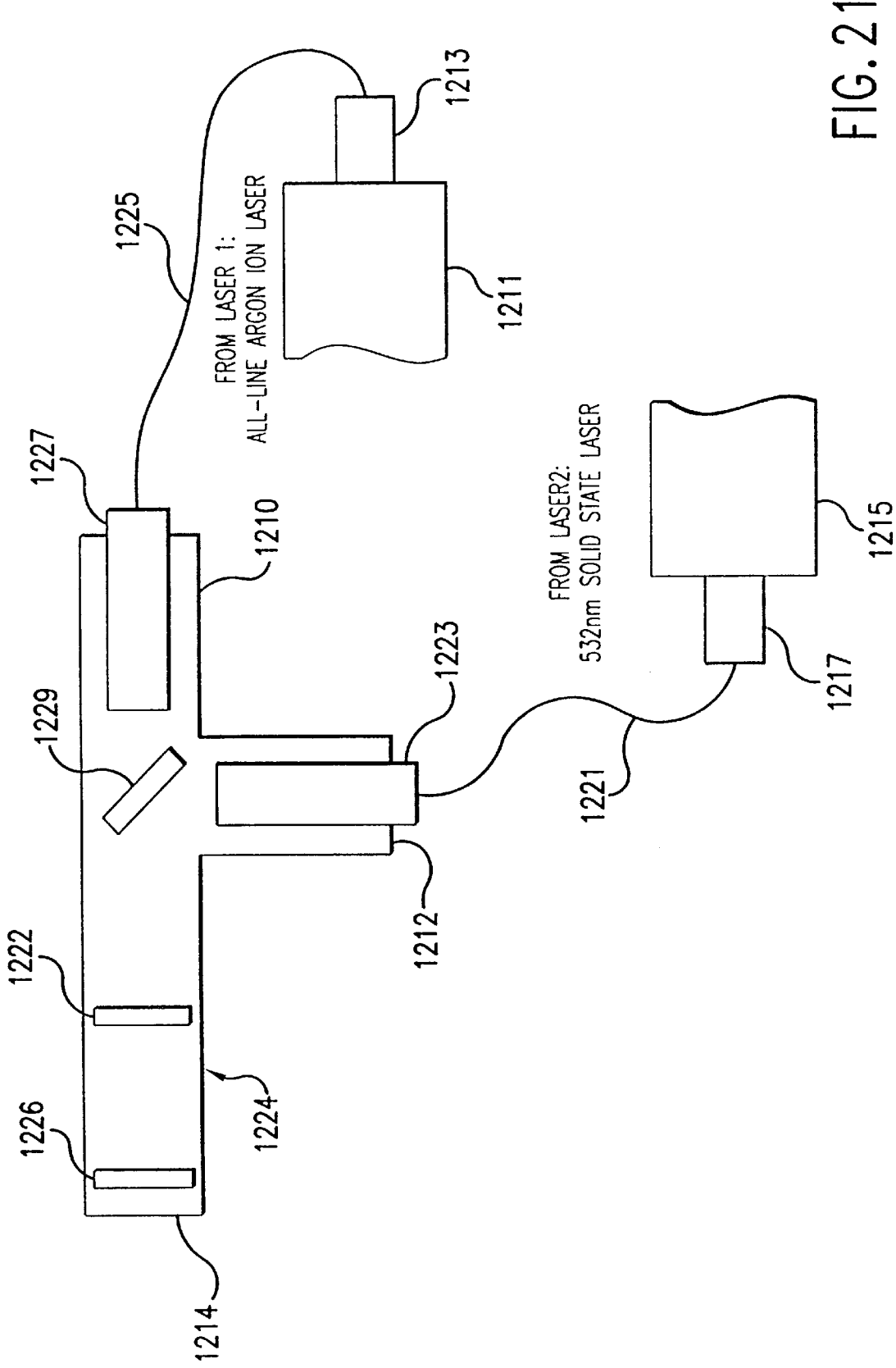
FIG. 21 shows a multi-wavelength beam generator using two laser heads.

FIG. 21 illustrates another embodiment of the multi-wavelength beam generator in which two laser heads 1211, 1215 are provided. The first laser head 1211 is identical with the laser head 1200; the second laser head 1217, however, generates different wavelength laser beam. The second laser head 1217 is preferably a solid state laser which produces laser beam with the wavelength longer than 532 nm. In an alternative embodiment, the second laser head 1217 produces multi-wavelength laser beams with the wavelengths different from the beam generated by the first laser head 1211.

In this embodiment, two optical coupling assemblies with fiber couplers 1213, 1217 and optical fiber cable 1225, 1221 are provided; the two optical coupling assemblies function identically with the optical coupling assembly 1202 of FIG. 20. The laser beams generated by the two laser heads 1211, 1215 and delivered by the optical coupling assemblies are combined in a laser emitter tube 1224 designed to receive laser beams from two laser sources.

The laser emitter tube 1224 has two input ends 1210, 1212 and one output end: a first fiber emitter tube 1227, receiving laser beams from the first laser head 1211, is located at the first input end 1210; a second fiber emitter tube 1223, receiving laser beams from the second laser 1215, is located at the second input end 1212; a one dimensional beam focuser 1226, preferably a positive cylindrical optical lens with 10 cm focal length and outputting the combined laser beams, is located at the output end 1214.

The laser beams received by the first and second fiber emitter tubes 1227, 1223 are combined by a dichroic filter 1229 which transmits laser beams received from the first fiber emitter tube 1227 and reflects the laser beams received from the second fiber emitter tube 1223, thereby combining the laser beams from the first and second fiber emitter tubes 1227, 1223.

A beam expander 1222, preferably a negative cylindrical optical lens 1222 with 1.5 cm focal length, is provided between the dichroic filter 1229 and the one-dimensional focuser 1226. The combination of the beam expander 1222 and the focuser 1226 optically function substantially identical to the optical processes described in FIG. 22 and FIGS. 22a–c.

In the preferred embodiment, polarization optics in the laser heads 1200, 1211, 1215 are removed to maximize the laser output power. The laser output power is increased by more than four times in the embodiment depicted in FIG. 21 with the combination of multi-line and unpolarized emission compared to a polarized single-line laser.

Figure 23:
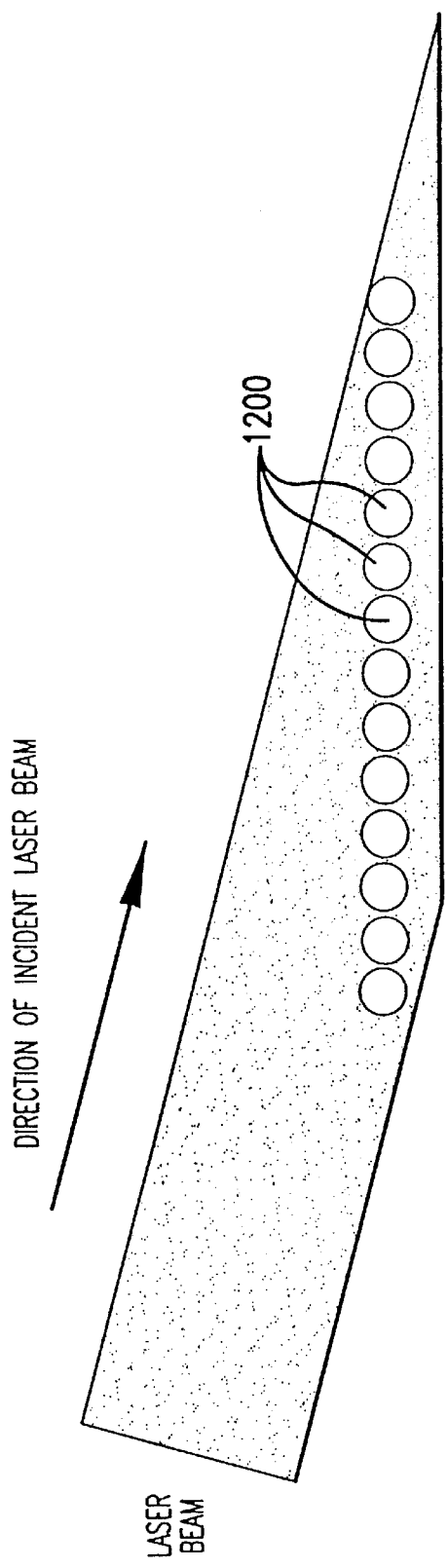
FIG. 23 shows the direction in which the light beam from a laser emitter tube impinges upon an array of capillary tubes.

Even though FIG. 22 depicts the resulting laser beam impinging upon the capillary array 1235 without any angle, a small angle entrance excitation configuration, as shown in FIG. 23, improves the excitation laser light coupling efficiency at the detection window. This also reduces the required laser power to excite a 96 (or more) capillary array and allows the use of a portable air-cooled argon ion laser in the DNA sequencer instrument. In other words, the multi-wavelength laser emitter tubes described in FIGS. 20 or 21 is aligned to illuminate a larger number of capillary array (such as 1000-capillaries) while preserving focusability of laser beams across a wide range of capillary array.

Figure 24:
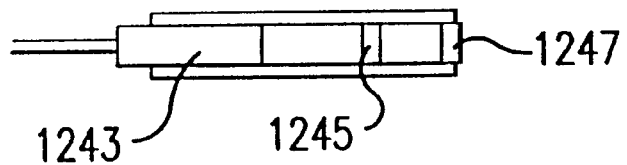
Figure 25:
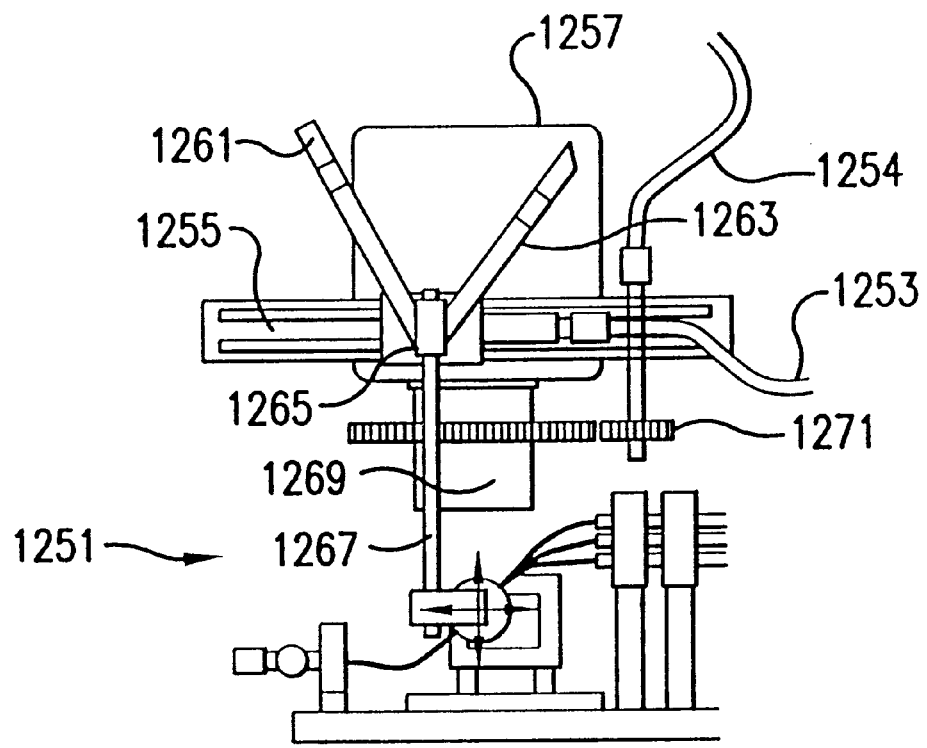
FIG. 25 shows structures around the detection region.

FIGS. 24 and 25 illustrate the integration of the CCD camera 1257 with the laser emitter tube 1243. In the preferred embodiment, the laser emitter tube 1243 is positioned perpendicular to the surface of the FIG. 25 with a small tilt angle so that the laser beam from the laser emitter tube 1243 impinges capillary array 1200 as shown in FIG. 23.

The laser emitter tube 1207 is positioned on a level with the capillary detection window with the beam emitting end of the tube 1207 facing away from the instrument operator. In the preferred embodiment, the laser emitter tube 1207 is secured to a bottom end of a tube control arm 1267 which is rotatably connected to an arm mount 1265. The arm mount 1265 is attached to the bottom ends of flexible rotators 1261, 1263. The top ends of the rotators in turn are connected to dials accessible from the exterior of the sequencer. The arm mount 1265 is also mounted on laser emitter positioning rails 1255 and moved by an arm mount position controller 1253. With the dials and the controller 1253 described above, the laser emitter tube 1207 is optimally positioned to deliver its output laser beam to the capillary array.

The CCD camera 1257 is mounted a camera mount (not shown in FIG. 25) which in turn is movably mounted on the laser emitter positioning rails 1255. A camera rotating cable (not shown in FIG. 25) moves the CCD camera plate in the horizontal direction on the rails 1255. A camera focus gear 1271 is connected to a gear control cable 1254 which controls the movements of the CCD camera lens assembly 1269. The preceding camera controllers allow the CCD camera 1257 to focus on the portion of capillary array impinged by the laser beam from the laser emitter tube 1243.

Figure 26:
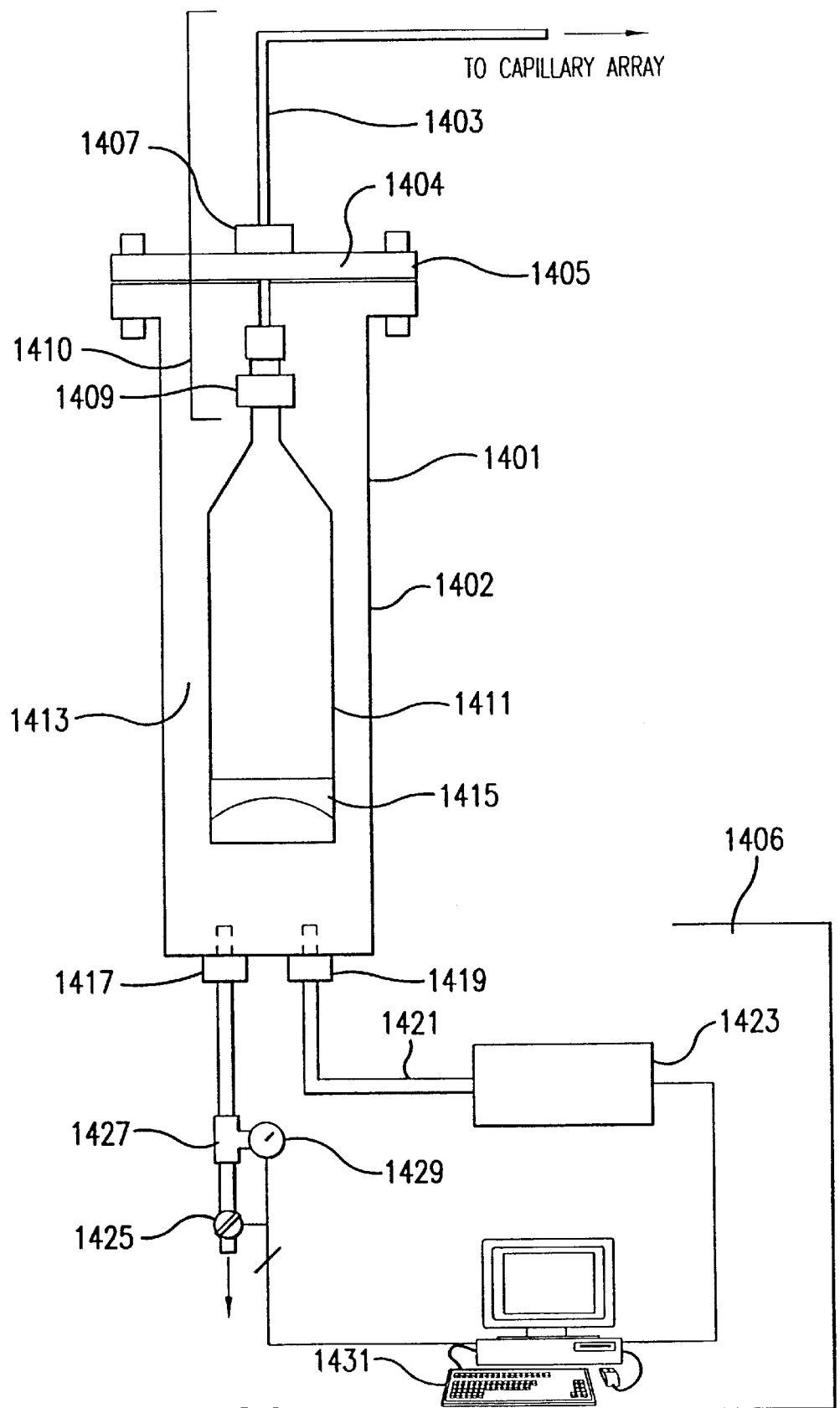
FIG. 26 shows a high pressure chamber which supplies high viscous gel.

Another preferred embodiment of the high viscosity liquid delivery system is illustrated in FIG. 26. The liquid delivery system has a high pressure chamber 1401 which holds low viscosity liquid 1413 such as water and a squeezable and disposable bag 1411 which contains a high viscosity liquid such as gel.

The chamber 1401 includes a cylinder 1402, preferably made from metallic material such as aluminum or stainless steel for sustaining interior pressures up to 2000 psi, has a substantially hollow body with a closed bottom and an open top. A cap 1404 is removably affixed to the top of the cylinder 1402, whereby the cylinder 1402 and the cap 1404 form the high pressure chamber 1401 to hold the liquid 1413 and the disposable bag 1411.

The gel container 1411 is removably attached to an outlet assembly 1410, preferably by a Swagelock 1409. The viscous liquid is forced out through the outlet assembly 1410 when the pressure inside the chamber increases. The outlet assembly 1410 is fitted to the cap 1404 with a water tight fitting 1407, available from Swagelock. The outlet assembly 1410 also includes a gel delivery tubing 1403. Because the pressure around the squeezable gel bag 1411 is uniformly applied by the liquid 1413, pressure rating requirement for the gel container is minimum. The gel bag 1411 is, therefore, economically made from a disposable bag with a large gel holding capacity sufficient for multiple gel runs.

The pressure inside the chamber 1401 is increased or decreased by a pressure control assembly 1406. When more liquid is supplied to the chamber 1401 by the pressure control assembly 1406, the pressure inside the chamber 1401 increases. When the pressure is increased by an excessive amount or when the cap 1404 is to be opened to replace the bag 1411, the liquid inside the chamber is released by the pressure control assembly to reduce the pressure.

The pressure control assembly includes a high pressure pump 1423 controlled by a controller 1404. In the preferred embodiment, the high pressure pump 1423 is another HPLC pump. The pressure control assembly 1406 also includes an inlet tubing 1421 connected to the pump 1423 and fitted to the bottom of the cylinder by a water tight fitting 1419.

An outlet tubing 1427 is also provided to the pressure control assembly 1406. The outlet tubing 1427 is fitted, preferably, to the bottom of the cylinder 1402 by a second water tight fitting 1417. In turn, the outlet tubing includes a release valve 1425 and a pressure transducer 1429 for generating a feedback signal, preferably less than 6 volts, which is communicated to the controller 1404. The release valve 1425 is controlled by the controller 1404.

The controller 1404 is preferably a part of the central computer controller 404 in FIG. 10 in order to save space; however, in alternative embodiments, the central computer controller 404 are replaced with other types of controllers such as another computer, microprocessor, or any other electronic device capable of controlling a water pump and a valve.

By monitoring the feedback signal, which indicates the pressure inside of the chamber 1401, the controller 1404 performs the following functions: (1) when the pressure inside the chamber 1401 needs to be increased by a certain amount, the controller 1404 activates the HPLC pump 1423 to pump more liquid into the chamber 1401 via the inlet tubing 1421; or (2) when the pressure inside the chamber 1401 needs to be decreased by a certain amount, the controller 1404 opens the releasing valve 1425 to release the liquid from the chamber 1401. Once a sufficient amount of gel is pushed out, the pump stops which caused the pressure inside the chamber to decrease and return the pressure to a previous equilibrium. The preferred gel filling pressure is 500 psi.

Figure 27:
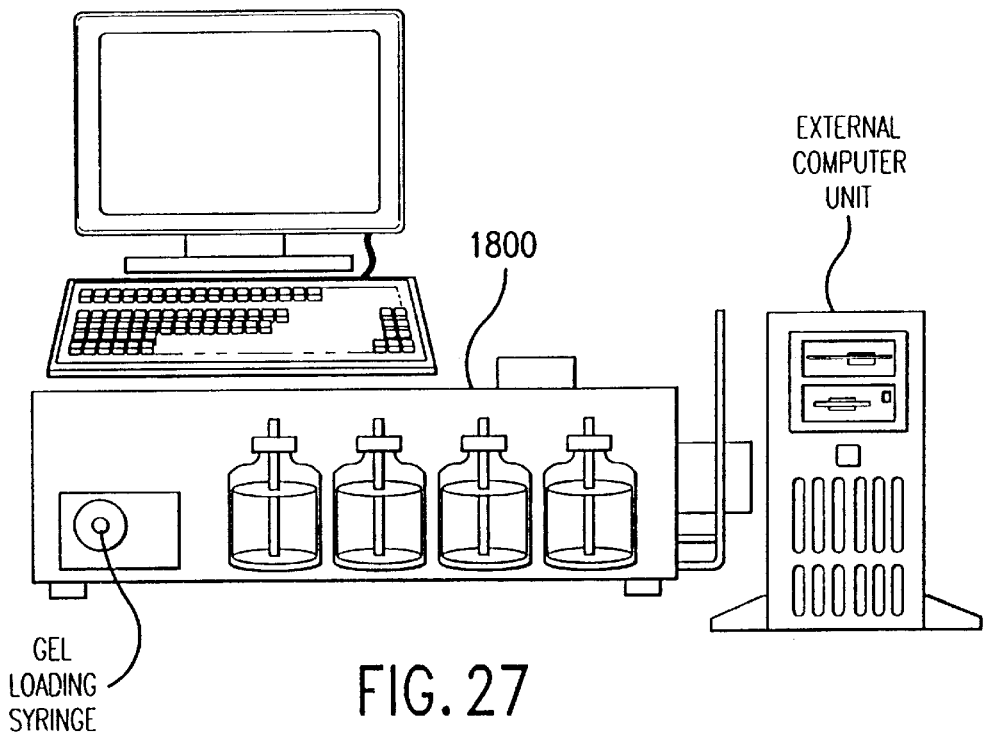
FIG. 27 shows a solvent/gel delivery module of the preferred embodiment.
Figure 28:
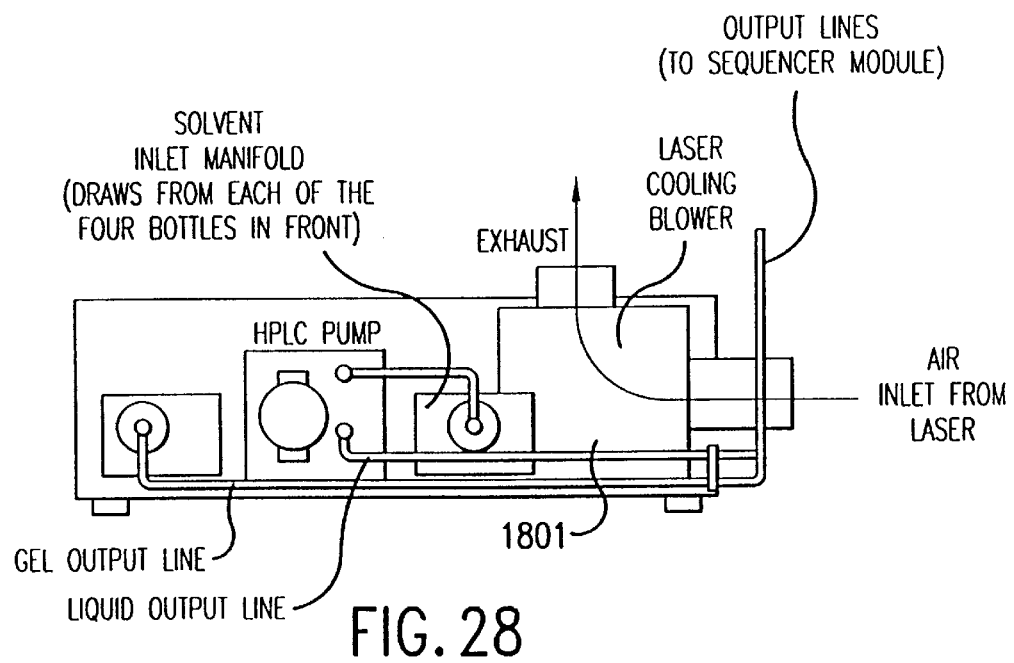
FIG. 28 shows a back view of the solvent/gel delivery module.

FIG. 27 illustrates the preferred embodiment of a solvent/gel delivery module 1800 which is used after a DNA analysis to recondition the capillary array and to refill the capillary array with gel. FIG. 28 shows a back view of the solvent/gel delivery module 1800. The solvent/gel delivery module 1800 is preferably placed next to the sequencer. The purpose of the solvent/gel delivery module 1800 is to provide sequential, automated gel delivery and capillary reconditioning.

Figure 29:
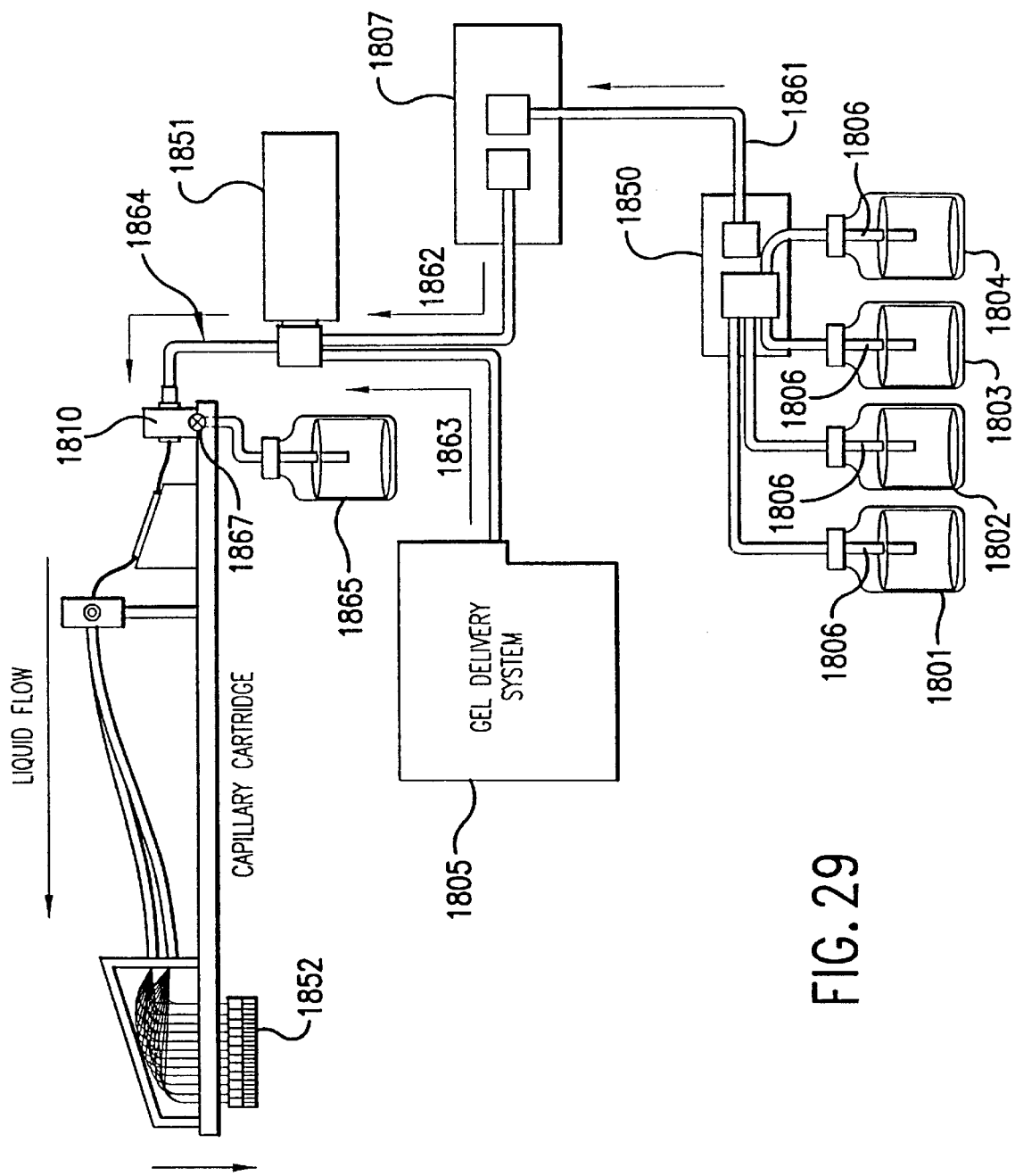
FIG. 29 shows the flow of gel and solvent through the solvent/gel delivery module in the preferred embodiment.

FIG. 29 illustrates the integration of the high pressure gel delivery system 1805, either the gel delivery syringe 804 in FIG. 16 or the high pressure chamber 1401 in FIG. 26, into the solvent/gel delivery module 1800 of FIG. 27. In this preferred embodiment, a solvent manifold 1850 connects four inlets from the feeder tubes 1806 of solvent containers 1801–1804 to an outlet. Feeder tubes 1806 from solvent containers 1801–1804, two bottles with methanol, a bottle with poly vinyl pyrrolidone (PVP), preferably 2% of PVP, and a bottle with a buffer solution, are connected to the inlets of the solvent manifold 1850. The inlet of the HPLC pump 1807 is connected to the outlet of the solvent manifold 1850 by a pump connecting tube 1861 and the outlet of the HPLC pump 1807 is connected to an inlet of a valve manifold 1851 by pump outlet tube 1862. An outlet from the HPLC pump 1807 (not shown in FIG. 29) is connected to the high pressure chamber 1805 as discussed above.

A valve manifold 1851 connects two inlets and an outlet. One inlet of the valve manifold 1851 is connected to the gel delivery system 1805 by a gel outlet tube 1863 and the other inlet of the valve manifold 1851 is connected to the outlet of the HPLC pump 1807. The outlet of the valve manifold 1851 is connected to a liquid delivery chamber 1810, preferably the high pressure T-fitting 1182 of FIG. 18, by a manifold outlet tube 1864. The liquid delivery chamber 1810 includes a chamber valve 1867 for draining waste in the liquid delivery chamber 1810 to a waste container 1865.

The controller 404 illustrated in FIG. 10 includes connections to the solvent manifold 1850, the HPLC pump 1807, the pressure control assembly for the gel delivery system 1805, the valve manifold 1851 and the chamber valve 1867 for controlling the connected components.

For example, the controller 404 controls the solvent manifold 1850 to a select solvent from the four solvent containers 1801–1804 and causes the valve manifold 1851 to select either the inlet connected to the chamber 1804 to receive the gel or the inlet connected to the HPLC pump 1807 to receive the solvent.

In the preferred embodiment, the lengths of the pump connecting tube 1861, the pump outlet tube 1862 and the manifold outlet tube 1864 are minimized to reduce wasting gel and solvents. In particular, the pump connecting and outlet tubes 1861, 1862 hold old solvent when new solvent is needed to be supplied to the valve manifold 1851, thereby requiring the old solvent to be wasted. The similar waste also occurs between the solvents and the gel in the manifold outlet tube 1864, which preferably is less than 50 cm and is more preferably less than 25 cm and is most preferably less than 10 cm.

As illustrated in FIG. 28, the solvent/gel module 1800 includes a blower 1801 for the laser head located in the sequencer. The laser head is housed in the bottom level of the sequencer module. The cooling blower is configured to essentially suck air out of the sequencer module and blow it out to the exhaust in the washing machine module 1800. The result is cold air moving across the laser, without creating huge amounts of turbulence in the sequencer module. A 5" diameter flexible hose is connected from the rear of the laser to the blower intake. The hot exhaust is carried out through another 5" diameter hose that is then connected to ceiling ductwork and expelled (not shown in FIG. 28).

Similar to the steps 700–703 of FIG. 13, the steps 1901, 1903 and 1905 of FIG. 31 explain the operation of the stacked, dual carrousel arrangement which was illustrated in FIG. 11, FIG. 12A. Since the steps are substantially identical to each other and the differences between them are self explanatory, no detailed explanations of the steps 1901, 1903 and 1905 is provided.

Figure 30:
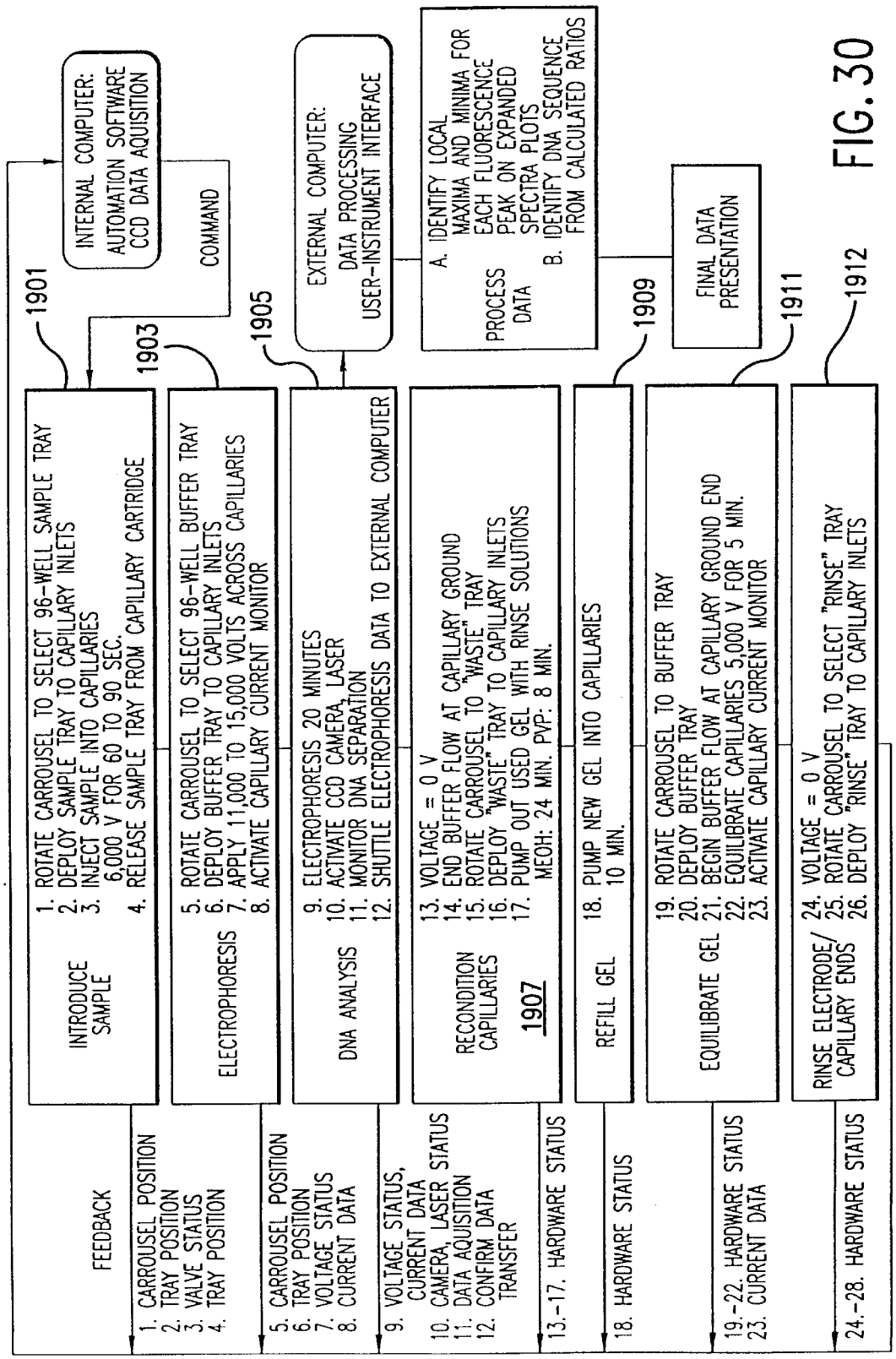
FIG. 30 shows a flowchart illustrating the operation of the preferred embodiment.

Furthermore, the steps 1907, 1909, 1911 and 1912 of FIG. 31 describe the operation of the solvent/gel delivery module 1800 which was illustrated in FIGS. 28–30. Since the operations of the solvent/gel delivery module 1800 is substantially identical to the operations of the solvent/gent module 800, duplicative discussions will be skipped. However, the different steps are discussed below.

In step 1907.17, the rinse step includes rinsing the capillary tubes with methanol for 24 minutes and, then, rinsing with PVP for 8 minutes. In step 1911.23, the current monitor attached between the current/monitoring board and the power supply is activated. In steps 1912.25 and 1912.26, a rinse tray is utilized for rinsing the first ends of the capillary tubes and the pins protruding from the current supply/monitoring board.

While the above invention has been described with reference to certain preferred embodiments, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. A capillary electrophoresis assembly comprising:
   at least eight capillaries, each capillary having a capillary first end and a capillary second end; and
   a fluid delivery apparatus connected to the capillary second ends, said fluid delivery apparatus comprising:
   a first valve manifold having a plurality of inlets and a first valve manifold outlet, said first valve manifold configured to selectively connect one of said plurality of inlets to said first valve manifold outlet;
   a first pump having a first pump inlet connected to the first valve manifold outlet, and a first pump outlet connected to a first supply line;
   a second valve manifold having a first inlet connected to said first supply line, a second inlet, and an outlet connected to a second supply line;
   a first chamber having three openings, a first opening connected to said second supply line, a second opening controlled by a chamber valve, and a third opening sealingly connected to said capillary second ends; and
   a controller configured to selectively operate the first valve manifold, the first pump, the second valve manifold and the chamber valve.

2. The assembly of claim 1, wherein the second supply line is less than 50 cm in length.

3. The assembly of claim 2, wherein the second supply line is less than 25 cm in length.

4. The assembly of claim 1, wherein the first pump and the first valve manifold comprise a single unit.

5. The assembly of claim 1, wherein the first chamber comprises a T-fitting.

6. The assembly of claim 1, wherein at least one container of a rinse solution and at least one container of a buffer solution are connected to first and second inputs, respectively, of said first valve manifold, and a container of gel is connected to the second inlet of the second valve manifold.

7. The assembly of claim 1, further comprising:
   a gel delivery system connected to the second inlet of the second valve manifold, said gel delivery system comprising:

a high pressure chamber having a first end provided with a chamber outlet and a second end provided with a chamber inlet, said high pressure chamber being occupied by a substantially incompressible medium;

a collapsible container positioned in said high pressure chamber and filled with a gel, said collapsible container being substantially surrounded by said medium, said collapsible container having an opening in communication with said chamber outlet;

a second pump connected to said chamber inlet and configured to selectively deliver additional medium into said high pressure chamber to thereby cause said collapsible container to at least partially collapse and force a predetermined quantity of said gel through the third opening of the first chamber and into said second capillary ends, when said chamber valve is closed and the second inlet of the second valve manifold is connected to the second supply line.

8. The assembly of claim 7, wherein the gel delivery system further comprises:

a pressure transducer arranged to sense a pressure of said medium and output a pressure signal reflective of said pressure;

a release valve connected to said high pressure chamber; and a controller configured to receive said pressure signal output by said pressure transducer and operate said release valve in response to said pressure signal.

9. A fluid delivery apparatus comprising:

a first valve manifold having a plurality of inlets and a first valve manifold outlet, said first valve mainfold configured to selectively connect one of said plurality of inlets to said first valve manifold outlet;

a first pump having a first pump inlet connected to the first valve manifold outlet, and a first pump outlet connected to a first supply line;

a second valve manifold having a first inlet connected to said first supply line, a second inlet, and an outlet connected to a second supply line;

a first chamber having three openings, a first opening connected to said second supply line, a second opening controlled by a chamber valve, and a third opening; and a controller configured to selectively operate the first valve manifold, the first pump, the second valve manifold and the chamber valve.

10. The fluid delivery apparatus of claim 9, wherein the second supply line is less than 50 cm in length.

11. The fluid delivery apparatus of claim 10, wherein the second supply line is less than 25 cm in length.

12. The fluid delivery apparatus of claim 9, wherein the first pump and the first valve manifold comprise a single unit.

13. The fluid delivery apparatus of claim 9, wherein the first chamber comprises a T-fitting.

14. The fluid delivery apparatus of claim 9, wherein at least one container of a rinse solution and at least one container of a buffer solution are connected to first and second inputs, respectively, of said first valve manifold, and a container of gel is connected to the second inlet of the second valve manifold.

15. The fluid delivery apparatus of claim 9, further comprising:

a gel delivery system connected to the second inlet of the second valve manifold, said gel delivery system comprising:

a high pressure chamber having a first end provided with a chamber outlet and a second end provided with a chamber inlet, said high pressure chamber being occupied by a substantially incompressible medium;

a collapsible container positioned in said high pressure chamber and filled with a gel, said collapsible container being substantially surrounded by said medium, said collapsible container having an opening in communication with said chamber outlet; and a second pump connected to said chamber inlet and configured to selectively deliver additional medium into said high pressure chamber to thereby cause said collapsible container to at least partially collapse and force a predetermined quantity of said gel through the third opening of the first chamber, when said chamber valve is closed and the second inlet of the second valve manifold is connected to the second supply line.

16. The fluid delivery apparatus of claim 15, wherein the gel delivery system further comprises:

a pressure transducer arranged to sense a pressure of said medium and output a pressure signal reflective of said pressure;

a release valve connected to said high pressure chamber; and a controller configured to receive said pressure signal output by said pressure transducer and operate said release valve in response to said pressure signal.

17. A method of simultaneously introducing fluids into at least eight capillaries, the capillaries having first ends and second ends, the method comprising:

providing a fluid delivery apparatus comprising:

a first valve manifold having a plurality of inlets and a first valve manifold outlet, said first valve manifold configured to selectively connect one of said plurality of inlets to said first valve manifold outlet;

a first pump having a first pump inlet connected to the first valve manifold outlet, and a first pump outlet connected to a first supply line;

a second valve manifold having a first inlet connected to said first supply line, a second inlet, and an outlet connected to a second supply line;

a first chamber having three openings, a first opening connected to said second supply line, a second opening controlled by a chamber valve, and a third opening connected to said second ends of said capillaries; and a controller configured to selectively operate the first valve manifold, the first pump, the second valve manifold and the chamber valve;

connecting a gel delivery system to the second inlet of said second valve manifold, said gel delivery system including a container of gel;

connecting a container of rinse solution to a first inlet of the first valve manifold;

connecting a container of buffer solution to a second inlet of the first valve manifold;

closing said chamber valve, if said chamber valve is not already closed;

adjusting a position of the second manifold to connect the gel delivery system to e second supply line via the second inlet of the second valve manifold, if said gel delivery system is not already connected to the second supply line, and activating said gel delivery system to thereby introduce gel into said capillaries via said capillary second ends.

18. The method of claim 17, further comprising:

closing said chamber valve, if said chamber valve is not already closed;

adjusting a position of the first valve manifold to connect the container of rinse solution to the first supply line via the first inlet of the first valve manifold;

adjusting a position of the second valve manifold to connect said first supply line to the second supply line via the first inlet of the second valve manifold, if said first supply line is not already connected to said second supply line; and activating said first pump to send rinse solution through the first and second supply lines into the chamber to thereby introduce rinse solution into said capillaries via said capillary second ends and force gel out of said capillaries through said capillary first ends.

19. The method of claim 17, further comprising:

opening the chamber valve, if said chamber valve is not already open;

adjusting a position of the first valve manifold to connect the container of buffer solution to the first supply line via the second inlet of the first valve manifold;

adjusting a position of the second value manifold to connect said first supply liene to the second supply line via the first inlet of the second valve manifold, if said first supply line is not already connected to said second supply line; and activating said first pump to send buffer solution through the first and second supply lines into the chamber to flow buffer solution past said second capillary ends during electrophoresis, said buffer solution exiting said chamber via said chamber valve.

20. The method of claim 19, further comprising:

closing said chamber valve, if said chamber valve is not already closed;

adjusting a position of the first valve manifold to connect the container of rinse solution to the first supply line via the first inlet of the first valve manifold;

adjusting a position of the second valve manifold to connect said first supply line to the second supply line via the first inlet of the second valve manifold, if said first supply line is not already connected to said second supply line; and activating said first pump to send rinse solution through the first and second supply lines into the chamber to thereby introduce rinse solution into said capillaries via said capillary second ends and force gel out of said capillaries through said capillary first ends.

* * * * *